(12) United States Patent
Ma et al.

(10) Patent No.: US 9,217,004 B2
(45) Date of Patent: *Dec. 22, 2015

(54) ORGANIC LIGHT EMITTING MATERIALS

(75) Inventors: Bin Ma, Plainsboro, NJ (US); Alan DeAngelis, Pennington, NJ (US); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 973 days.

This patent is subject to a terminal disclaimer.

(21) Appl. No.: 13/301,179

(22) Filed: Nov. 21, 2011

(65) Prior Publication Data

US 2013/0126831 A1   May 23, 2013

(51) Int. Cl.
| | |
|---|---|
| *H01L 51/54* | (2006.01) |
| *C09K 11/06* | (2006.01) |
| *C07F 15/00* | (2006.01) |
| *H01L 51/00* | (2006.01) |
| *H01L 51/50* | (2006.01) |

(52) U.S. Cl.
CPC ............. *C07F 15/0033* (2013.01); *C09K 11/06* (2013.01); *H01L 51/0085* (2013.01); *C09K 2211/1029* (2013.01); *C09K 2211/185* (2013.01); *H01L 51/001* (2013.01); *H01L 51/0081* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |

(Continued)

FOREIGN PATENT DOCUMENTS

| | | |
|---|---|---|
| CN | 1589307 A | 3/2005 |
| CN | 101160370 A | 4/2008 |

(Continued)

OTHER PUBLICATIONS

Kuwabara, Yoshiyuki et al., "Thermally Stable Multilayered Organic Electroluminescent Devices Using Novel Starburst Molecules, 4,4′,4″-Tri(N-carbazolyl)triphenylamine (TCTA) and 4,4′,4″-Tris(3-methylphenylphenyl-amino)triphenylamine (m-MTDATA), as Hole-Transport Materials," *Adv. Mater.*, 6(9):677-679 (1994).

(Continued)

*Primary Examiner* — Marie R. Yamnitzky
(74) *Attorney, Agent, or Firm* — Duane Morris LLP

(57) ABSTRACT

Novel phosphorescent metal complexes containing 2-phenylquinoline ligands with at least two substituents on the quinoline ring are provided. The disclosed compounds have low sublimation temperatures that allow for ease of purification and fabrication into a variety of OLED devices.

23 Claims, 3 Drawing Sheets

Formula I

(56) References Cited

U.S. PATENT DOCUMENTS

| | | | |
|---|---|---|---|
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 8,492,006 B2 * | 7/2013 | Ma et al. | 428/690 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0261076 A1 | 10/2008 | Kwong et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0085476 A1 | 4/2009 | Park et al. | |
| 2009/0101870 A1 | 4/2009 | Prakash et al. | |
| 2009/0104472 A1 | 4/2009 | Je et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2012/0181511 A1 * | 7/2012 | Ma et al. | 257/40 |

FOREIGN PATENT DOCUMENTS

| | | |
|---|---|---|
| CN | 101397311 A | 4/2009 |
| CN | 101657518 A | 2/2010 |
| EP | 0650955 | 5/1995 |
| EP | 1725079 | 11/2006 |
| EP | 1783132 | 5/2007 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| KR | 20110077173 | 7/2011 |
| WO | WO 01/39234 | 5/2001 |
| WO | WO 02/02714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru[II] PHosphorescent Emitters," *Adv. Mater.*, 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi et al., "Highly Efficient Phosphorescence From Organic Light-Emitting Devices with an Exciton-Block Layer," *Appl. Phys. Lett.*, 79(2):156-158 (2001).

(56) References Cited

OTHER PUBLICATIONS

Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al.,"A Novel Class of Phosphorescent Gold(III) Alkynyl-Based Organic Light-Emitting Devices with Tunable Colour," *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota,Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).
Sakamoto,Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al.,"1,2,4-Triazole Derivative as an Electron Transport Layer in Organic Electroluminescent Devices," *Jpn. J. Appl. Phys.*, 32:L917-L920 (1993).
Van Slyke, S. A. et al., "Organic Electroluminescent Devices with Improved Stability," *Appl. Phys. Lett.*, 69(15 ):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).
Baldo et al., "Highly Efficient Phosphorescent Emission from Organic Electroluminescent Devices," *Nature*, vol. 395, 151-154, (1998).
Baldo et al., "Very high-efficiency green organic light-e fitting devices based on electrophosphorescence," Appl. Phys. Lett., vol. 75, No. 1, 4-6 (1999).
European Search Report dated Mar. 6, 2013 for corresponding EP Application No. 12192327.0.
Chinese Patent Office, Notification of the First Office Action and English Version of Chinese Office Action regarding corresponding Chinese Application No. 201210489574.0 issued Apr. 1, 2015, pp. 1-14, including English translation.
Chinese Patent Office, Chinese Search Report regarding corresponding Chinese Application No. 201210489574.0 issued Apr. 1, 2015, pp. 1-4, including English translation.

\* cited by examiner

Formula I

ORGANIC LIGHT EMITTING MATERIALS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to metal complexes containing heterocyclic ligands with at least two substituents on the heterocyclic ligand. These metal complexes are suitable for use in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

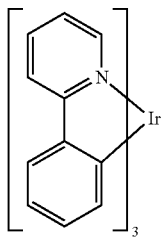

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the formula:

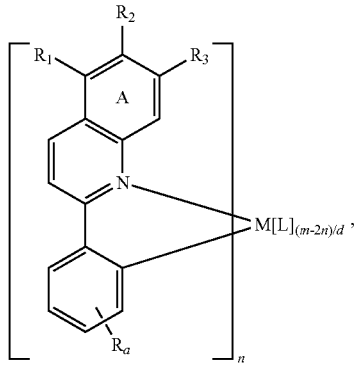

Formula I is provided.

M is a metal having an atomic weight higher than 40, L is a second ligand, m is the maximum coordination number of the metal M, d is the denticity of L, and n is at least 1.

Each of $R_1$, $R_2$ and $R_3$ is independently selected from the group consisting of hydrogen, deuterium, alkyl, silyl, germyl, cycloalkyl, and combinations thereof. At least two of $R_1$, $R_2$ and $R_3$ are not hydrogen or deuterium. The sum of the number of carbon atoms in $R_1$, $R_2$ and $R_3$ is at least 4, and any carbon atom in $R_1$, $R_2$, or $R_3$ attached directly to ring A is a primary, a secondary, or a tertiary carbon atom. $R_a$ represents mono-, di-, tri-, or tetra-substitution, and $R_a$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound has the formula:

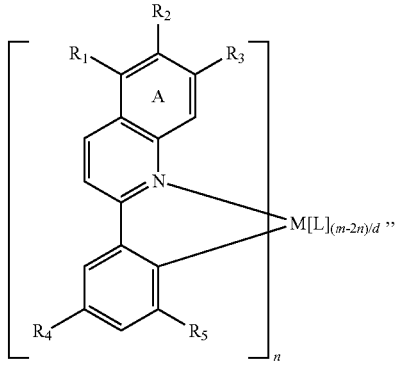

Formula II wherein $R_4$ and $R_5$ are alkyl.

In one aspect, the compound has the formula:

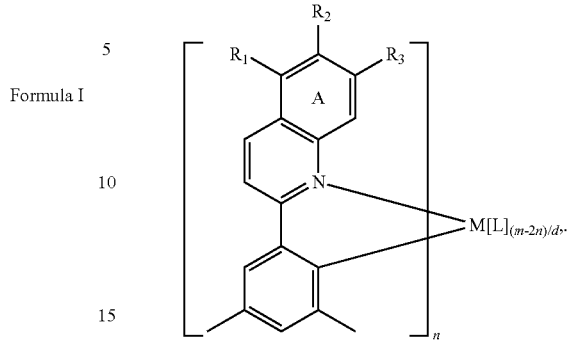

Formula III

In one aspect, M is Ir.
In one aspect, n is 2. In one aspect, L is a monoanionic bidentate ligand. In another aspect, L is

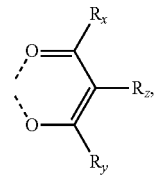

and $R_x$, $R_y$, and $R_z$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $R_x$, $R_y$, and $R_z$ are independently selected from the group consisting of alkyl, hydrogen, deuterium, and combinations thereof. In one aspect, $R_z$ is hydrogen or deuterium, and $R_x$ and $R_y$ are independently selected from the group consisting of methyl, $CH(CH_3)_2$, and $CH_2CH(CH_3)_2$. In one aspect, the compound has the formula:

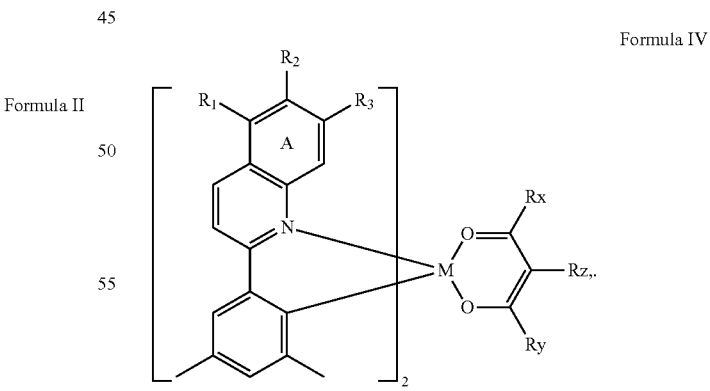

Formula IV

In one aspect, $R_1$ and $R_3$ are alkyl. In one aspect, $R_1$ and $R_2$ are alkyl. In one aspect, $R_2$ and $R_3$ are alkyl. In one aspect, $R_1$ and $R_3$ are silyl or germyl. In one aspect, $R_1$, $R_2$ and $R_3$ are independently selected from the group consisting of: $CH(CH_3)_2$, $CH_2CH(CH_3)_2$, $CH_2C(CH_3)_3$, cyclopentyl, cyclohexyl, ethyl, trimethylsilyl, triethylsilyl, triisopropylsilyl, trimethylgermyl, triethylgermyl, and triisopropylgermyl.

In one aspect, the compound is selected from the group consisting of Compound 1-Compound 60.

In one aspect, a first device is provided. The first device comprises a first organic light emitting device, further comprising: an anode, a cathode, and an organic layer, disposed between the anode and the cathode, comprising a compound having the formula:

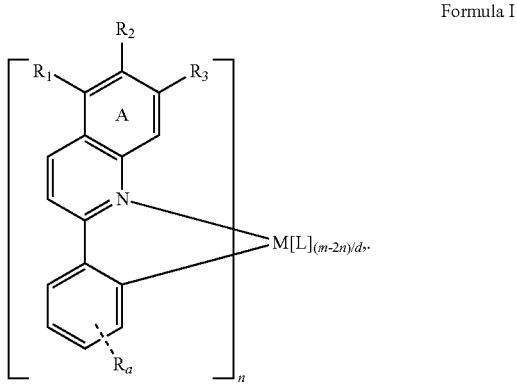

Formula I

M is a metal having an atomic weight higher than 40, L is a second ligand, m is the maximum coordination number of the metal M, d is the denticity of L, and n is at least 1.

Each of $R_1$, $R_2$ and $R_3$ is independently selected from the group consisting of hydrogen, deuterium, alkyl, silyl, germyl, cycloalkyl, and combinations thereof. At least two of $R_1$, $R_2$ and $R_3$ are not hydrogen or deuterium. The sum of the number of carbon atoms in $R_1$, $R_2$ and $R_3$ is at least 4, and any carbon atom in $R_1$, $R_2$, or $R_3$ attached directly to ring A is a primary, a secondary, or a tertiary carbon atom. $R_a$ represents mono-, di-, tri-, or tetra-substitution, and $R_a$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the first device is a consumer product. In another aspect, the first device is an organic light-emitting device.

In one aspect, the first device comprises a lighting panel. In one aspect, the organic layer is an emissive layer and the compound is a non-emissive dopant. In one aspect, the organic layer further comprises a host.

In one aspect, the host is a metal 8-hydroxyquinolate.
In one aspect, the host is:

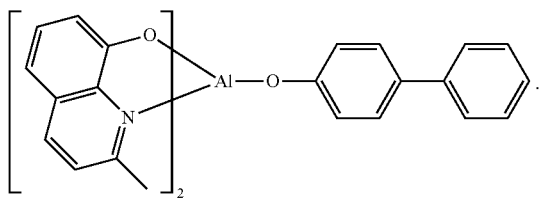

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
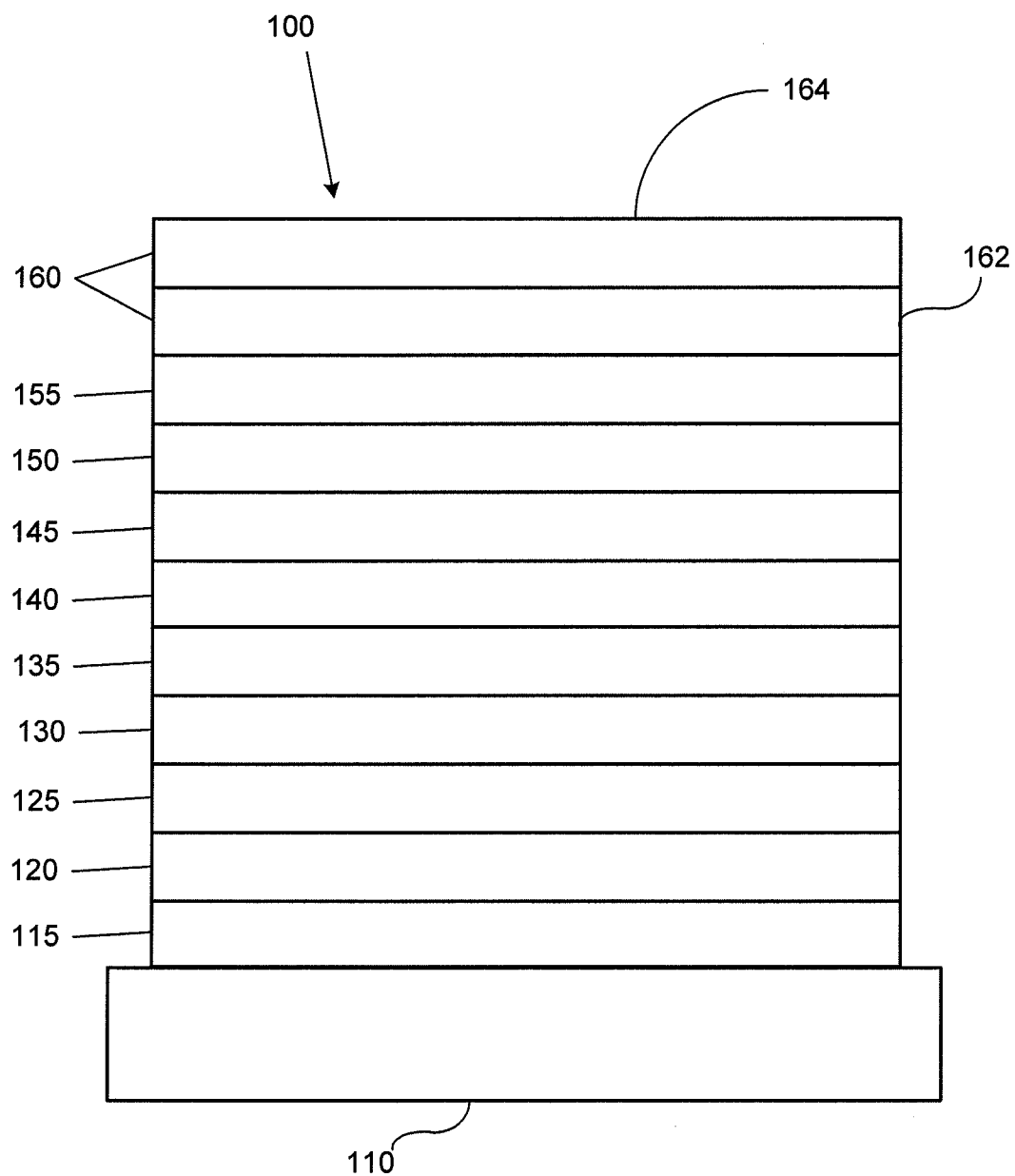
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
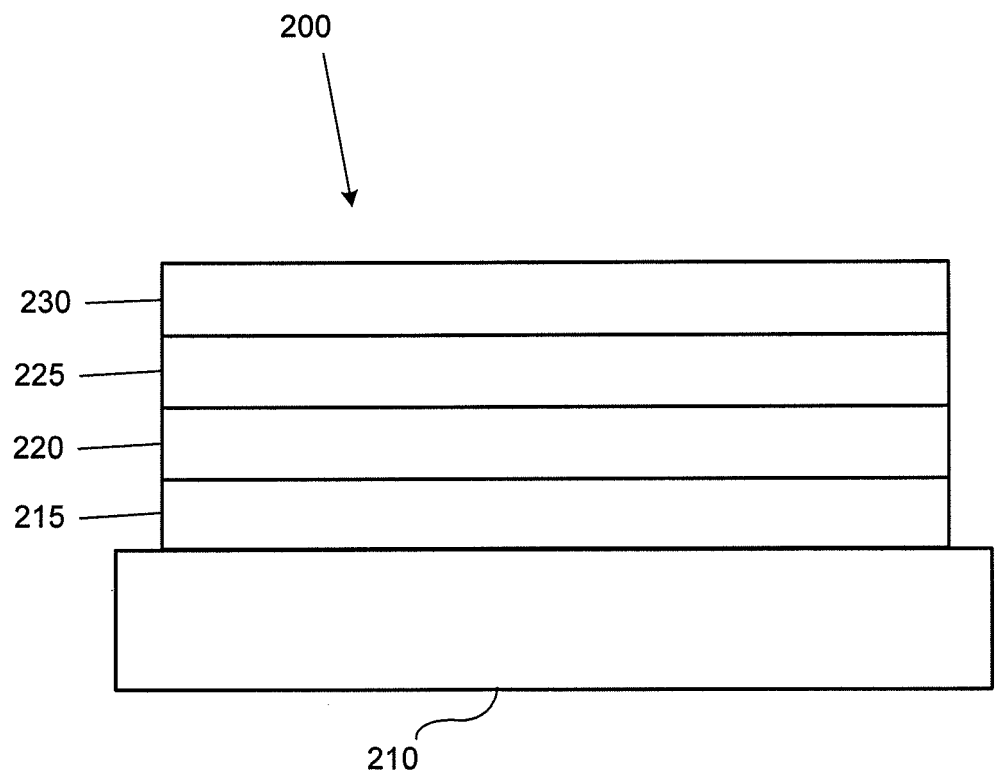
FIG. 2 shows an inverted organic light emitting device that does not have a separate electron transport layer.
Figure 3:
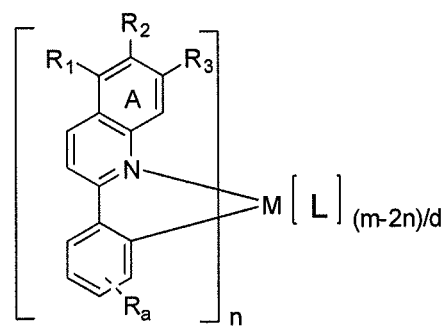
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the formula:

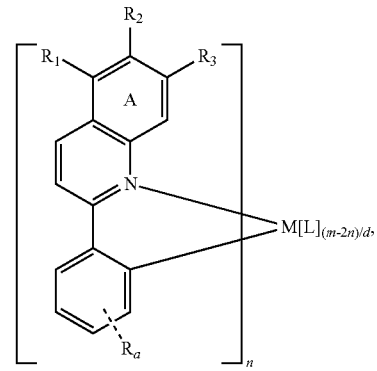

Formula I, is provided.

M is a metal having an atomic weight higher than 40, L is a second ligand, m is the maximum coordination number of the metal M, d is the denticity of L, and n is at least 1. By "denticity" it is meant that d numerically represents the number of bonds a second ligand L makes with metal M. Thus, if L is a monodentate ligand, then d is 1, if L is a bidentate ligand, d is 2, etc.

Each of $R_1$, $R_2$ and $R_3$ is independently selected from the group consisting of hydrogen, deuterium, alkyl, silyl, germyl, cycloalkyl, and combinations thereof. At least two of $R_1$, $R_2$ and $R_3$ are not hydrogen or deuterium. The sum of the number of carbon atoms in $R_1$, $R_2$ and $R_3$ is at least 4, and any carbon atom in $R_1$, $R_2$, or $R_3$ attached directly to ring A is a primary, a secondary, or a tertiary carbon atom. $R_a$ represents mono-, di-, tri-, or tetra-substitution, and $R_a$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

It has been unexpectedly discovered that alkyl substitution at two or more of positions $R_1$ through $R_3$ results in compounds of Formula I with desirable properties. These properties enable OLED devices that incorporate compounds of Formula I to have improved properties such as higher efficiency and longer lifetime. Alkyl substitution at two or more of positions $R_1$ through $R_3$ also results in compounds with lowered sublimation temperatures despite the fact that these compounds have higher molecular weights than compounds with all hydrogen substitution at $R_1$ through $R_3$. Without being bound by theory, it is believed that this decrease in sublimation temperature may be the result of decreased or less efficient molecular stacking in the solid state, thereby decreasing the energy required to disrupt the crystal lattice and resulting in decreased sublimation temperatures. Lower sublimation temperatures advantageously allow for easier purification of compounds of Formula I and better thermal stability in manufacturing.

Additionally, it has been surprisingly discovered that when any carbon atom in $R_1$, $R_2$, or $R_3$ attached directly to ring A is a primary, a secondary, or a tertiary carbon atom, the compounds are more stable in OLED devices than if a quaternary carbon is directly attached to ring A. Without being bound by theory, it is believed that an alkyl group bearing a quaternary carbon center, such as a t-butyl group directly connected to the aromatic part of the ligand, is prone to de-alkylation owing to the relatively high stability of the t-butyl carbocation, which is believed to form during regular OLED operation when such groups are attached to compounds of Formula I or to similar compounds. This facile de-alkylation is believed to have a detrimental effect on OLED operation resulting in decreased device lifetime.

In one embodiment, the compound has the formula:

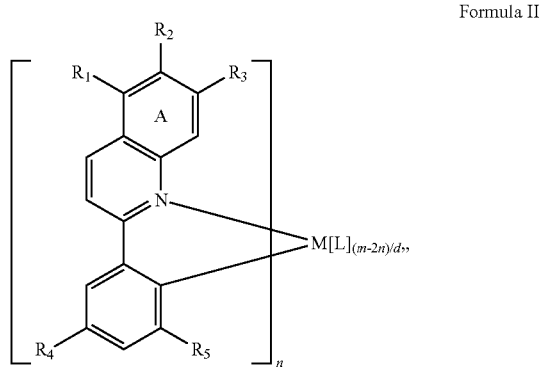

Formula II wherein $R_4$ and $R_5$ are alkyl.

In one embodiment, the compound has the formula:

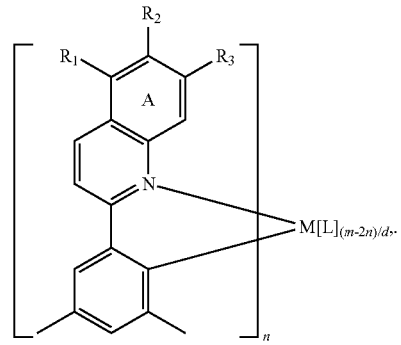

Formula III

In one embodiment, M is Ir.

In one embodiment, L is a monoanionic bidentate ligand.

In another embodiment, L is

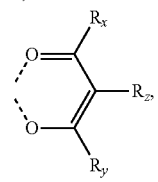

and $R_x$, $R_y$, and $R_z$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $R_x$, $R_y$, and $R_z$ are independently selected from the group consisting of alkyl, hydrogen, deuterium, and combinations thereof. In one embodiment, $R_z$ is hydrogen or deuterium, and $R_x$ and $R_y$ are independently selected from the group consisting of methyl, $CH(CH_3)_2$, and $CH_2CH(CH_3)_2$. In one embodiment, the compound has the formula:

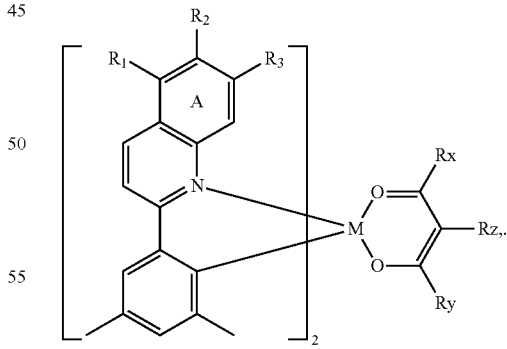

Formula IV

In one embodiment, $R_1$ and $R_3$ are alkyl. In one aspect, $R_1$ and $R_2$ are alkyl. In one embodiment, $R_2$ and $R_3$ are alkyl. In one embodiment, $R_1$ and $R_3$ are silyl or germyl. In one embodiment, $R_1$, $R_2$ and $R_3$ are independently selected from the group consisting of: $CH(CH_3)_2$, $CH_2CH(CH_3)_2$, $CH_2C(CH_3)_3$, cyclopentyl, cyclohexyl, ethyl, trimethylsilyl, triethylsilyl, triisopropylsilyl, trimethylgermyl, triethylgermyl, and triisopropylgermyl.

In one embodiment, the compound is selected from the group consisting of:
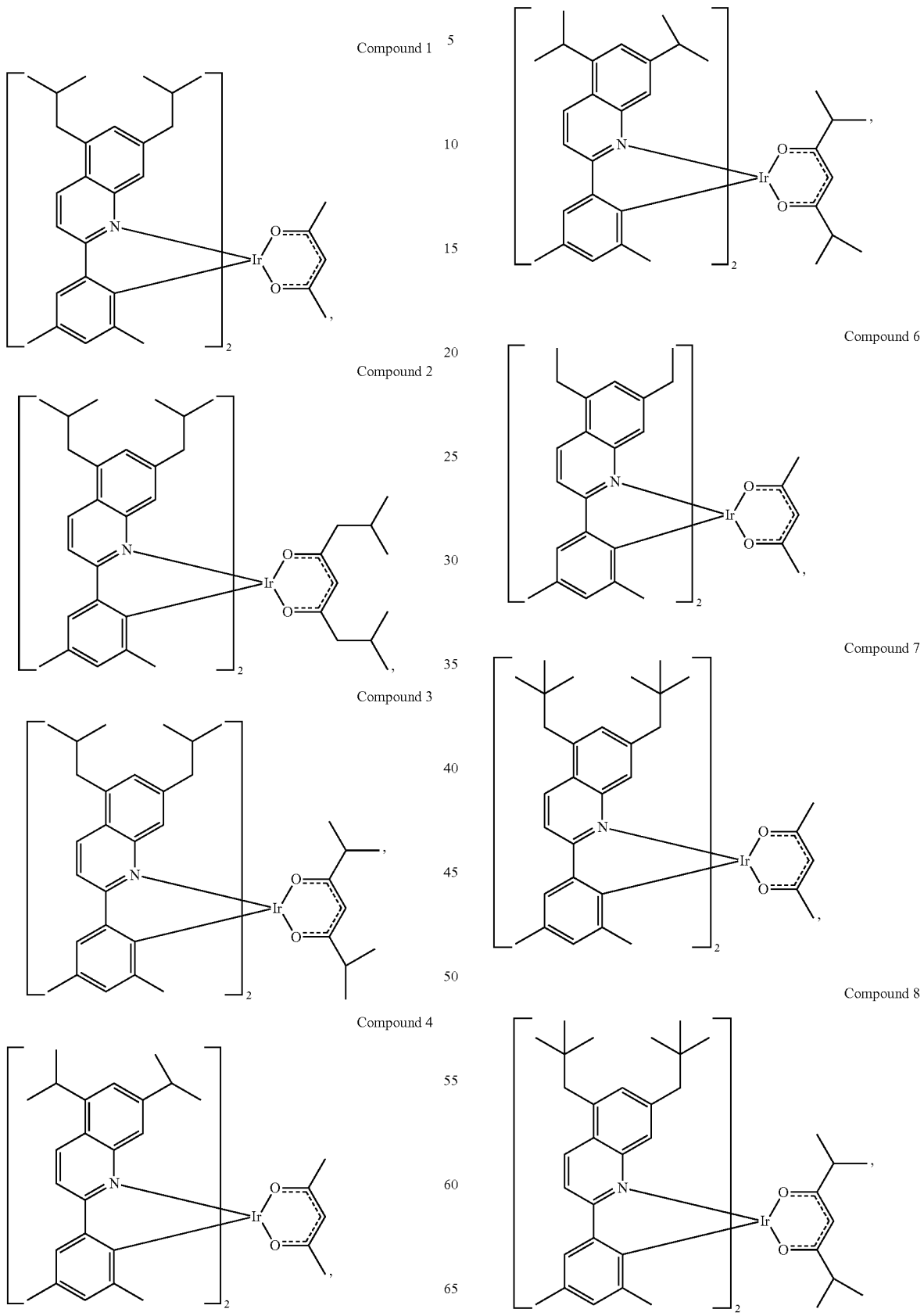

Compound 9
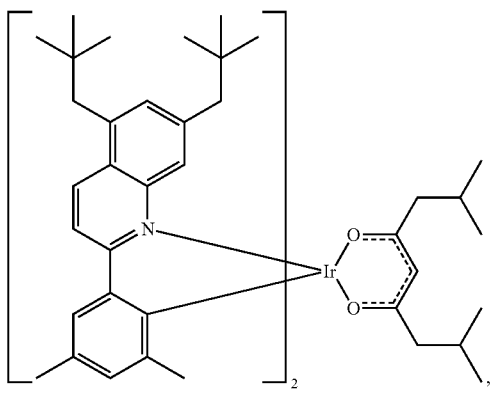
Compound 10
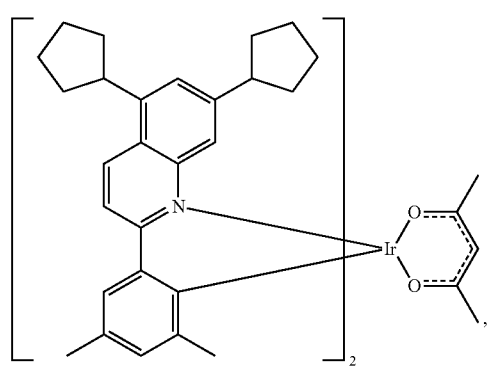
Compound 11
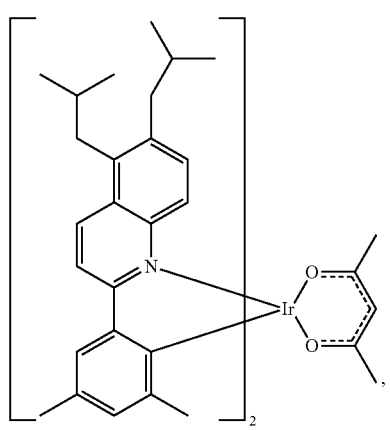
Compound 12
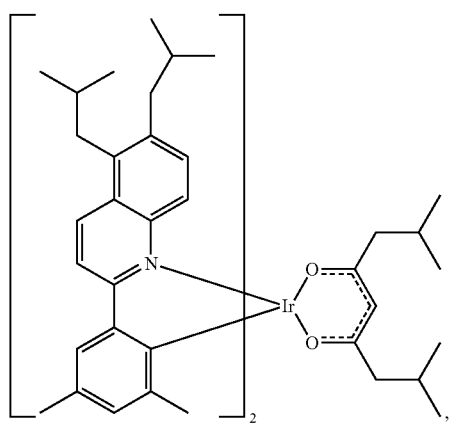
Compound 13
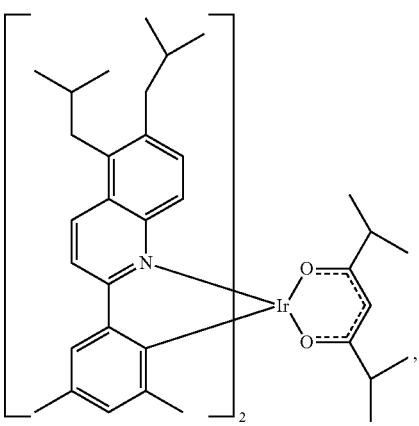
Compound 14
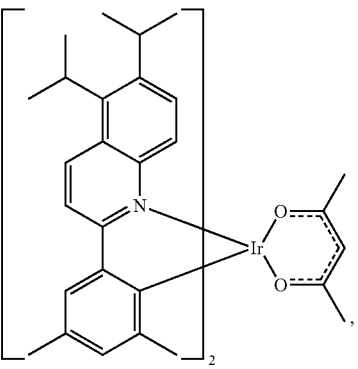
Compound 15
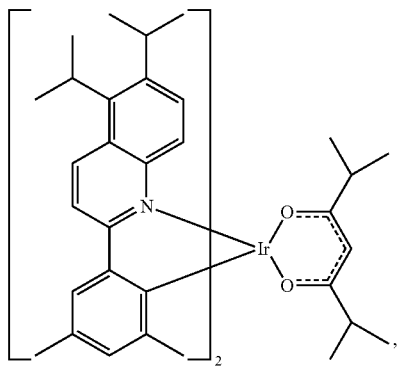

Compound 16
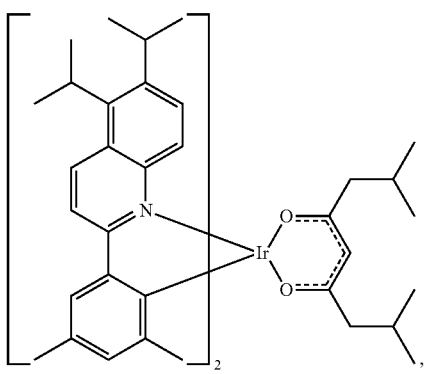
Compound 17
Compound 18
Compound 19
Compound 20
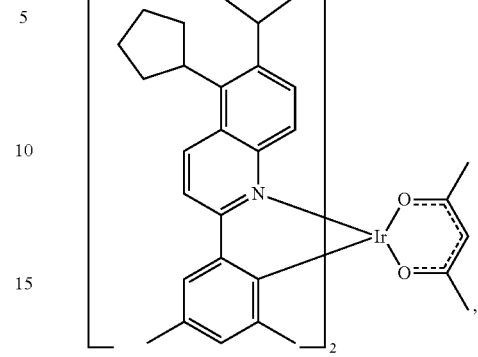
Compound 21
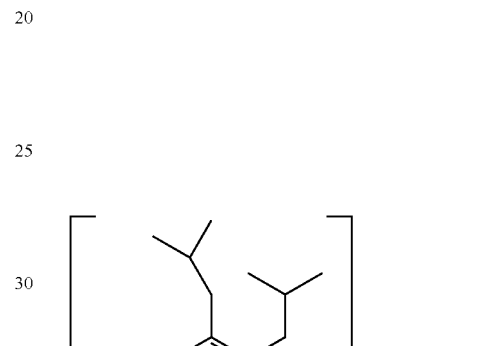
Compound 22
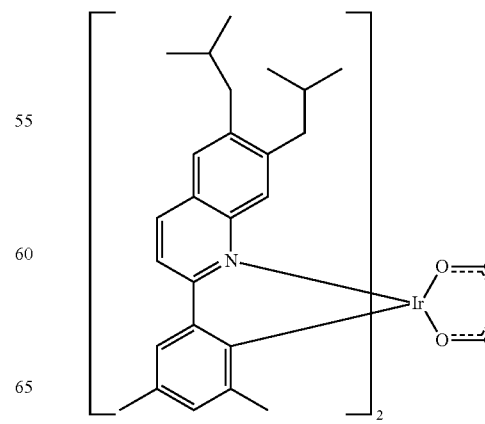

Compound 23
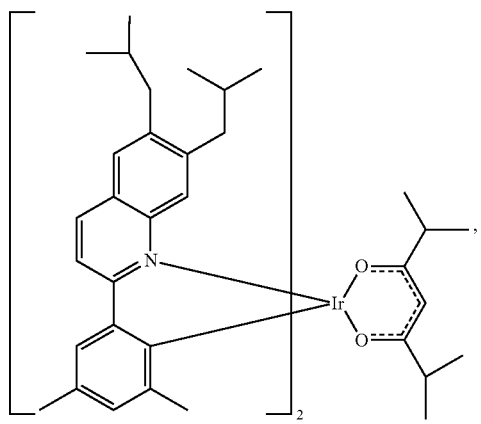
Compound 24
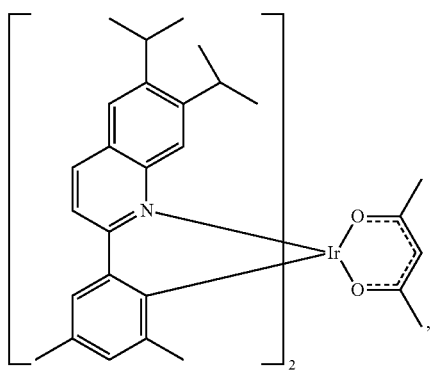
Compound 25
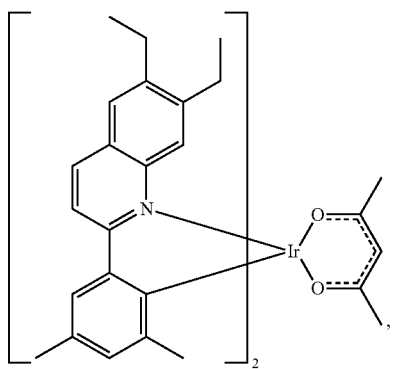
Compound 26
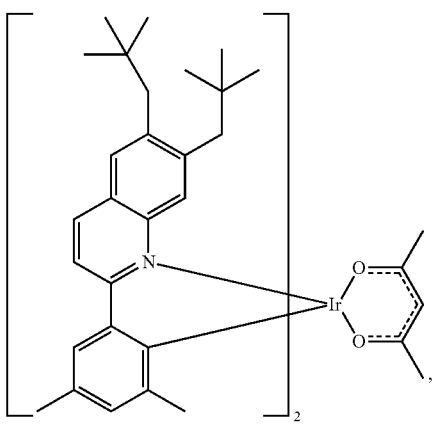
Compound 27
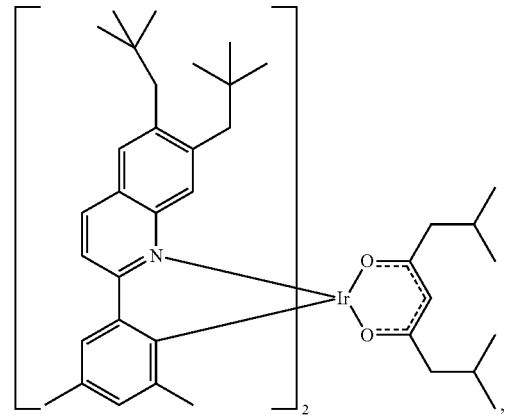
Compound 28
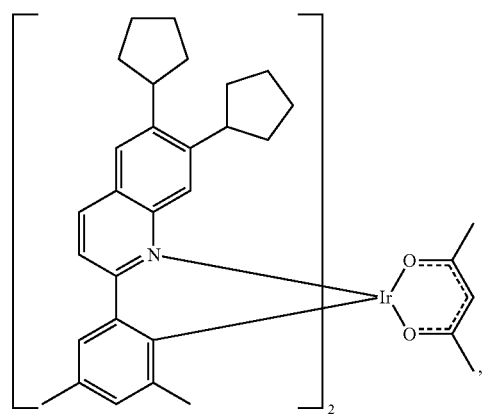
Compound 30
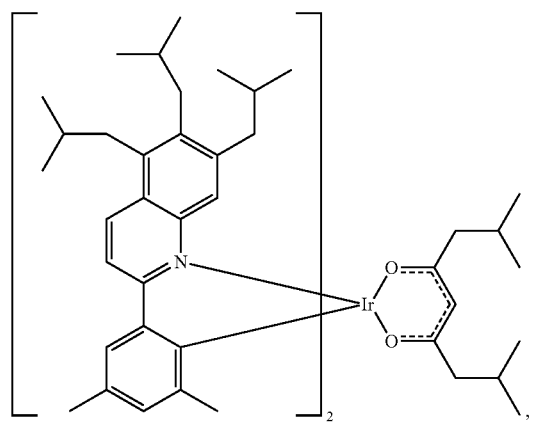

Compound 31
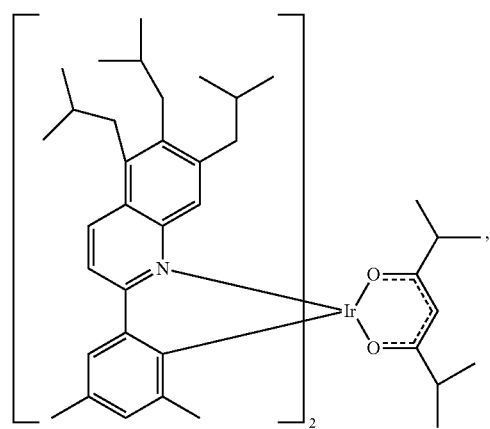
Compound 32
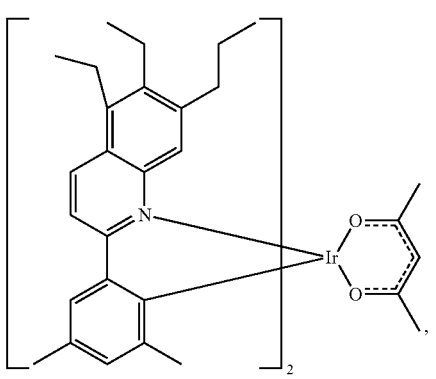
Compound 33
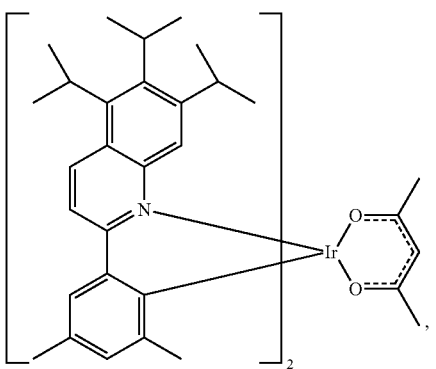
Compound 34
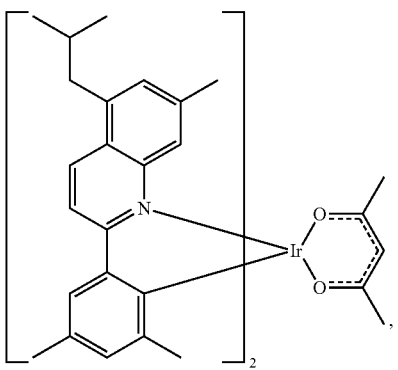
Compound 35
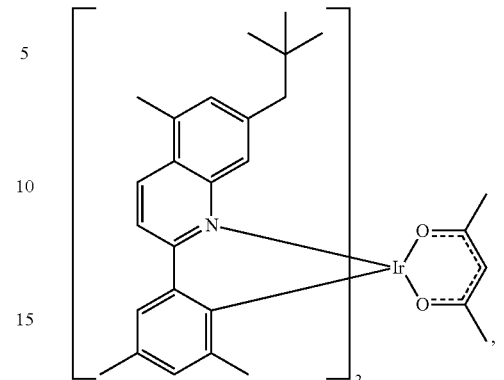
Compound 36
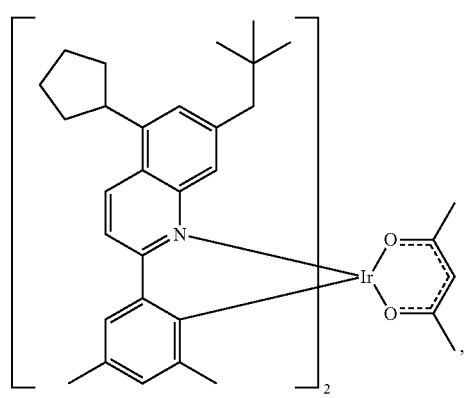
Compound 37
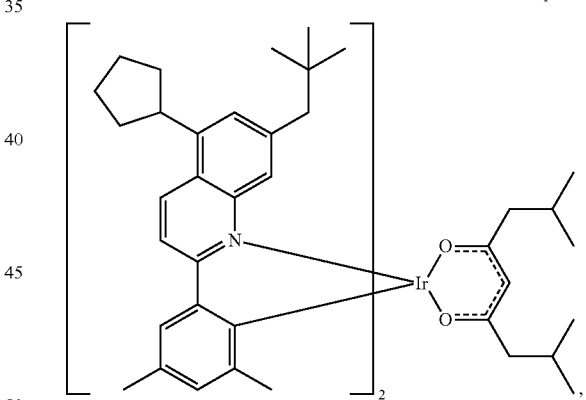
Compound 38
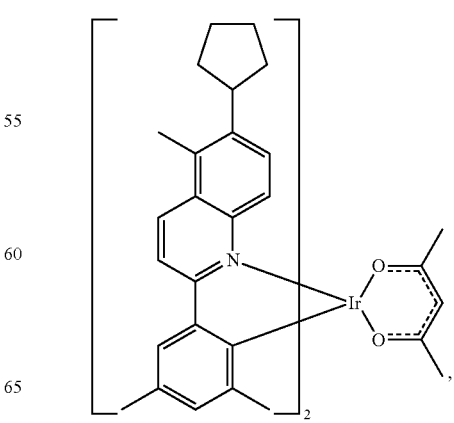

Compound 39
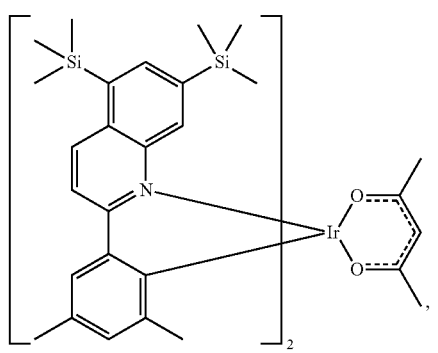
Compound 40
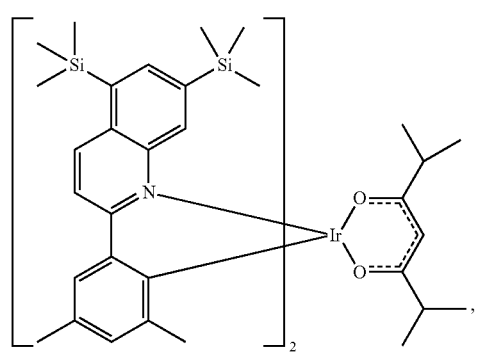
Compound 41
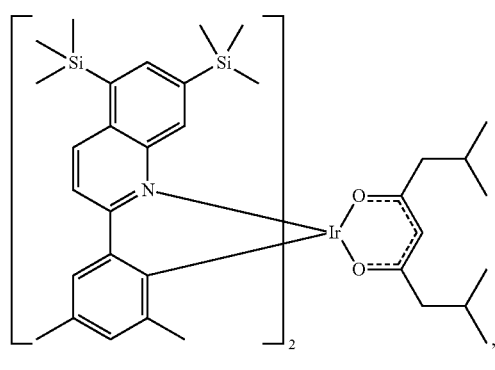
Compound 42
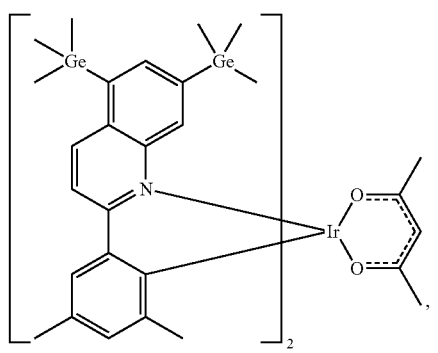
Compound 43
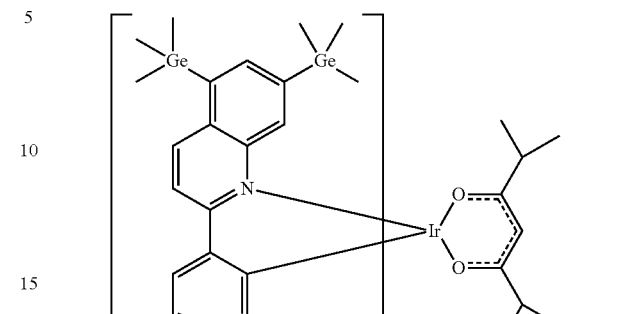
Compound 44
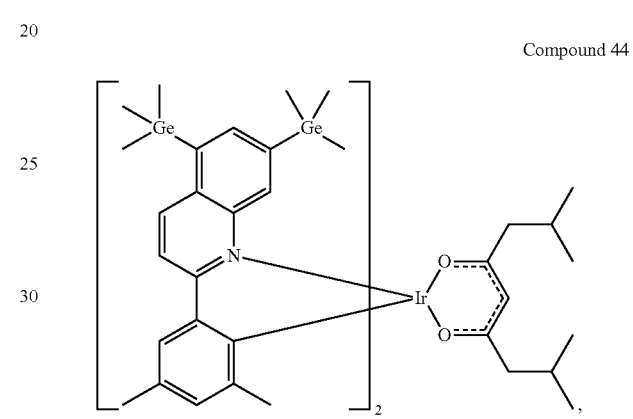
Compound 45
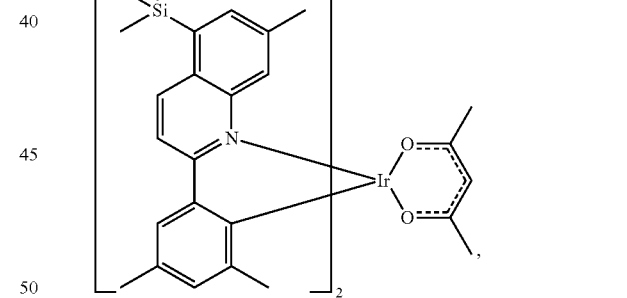
Compound 46
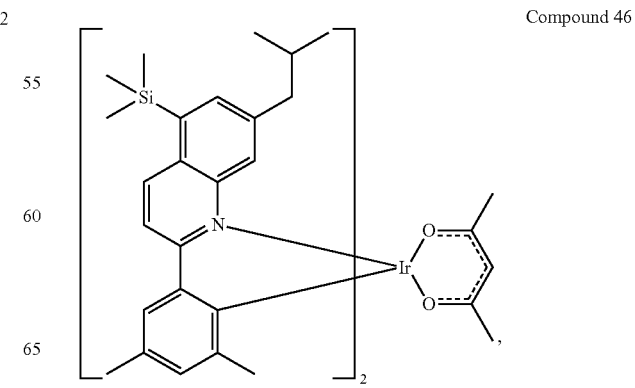

Compound 47
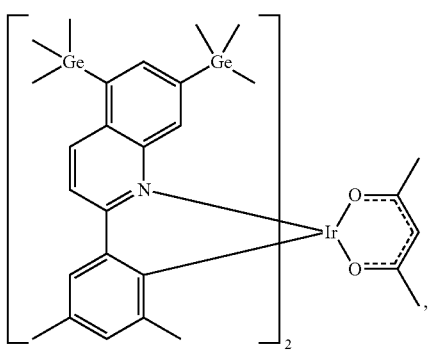
Compound 48
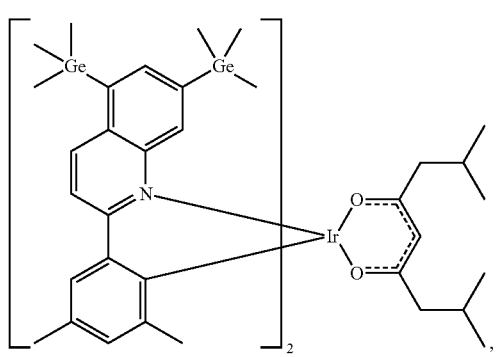
Compound 49
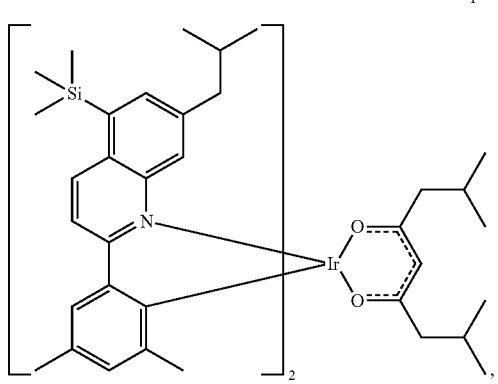
Compound 50
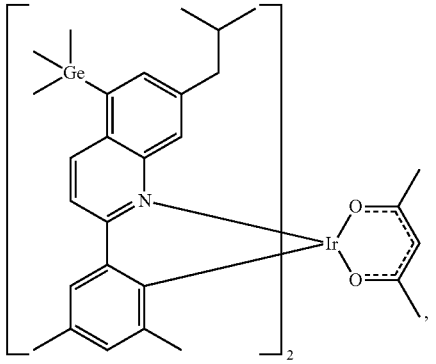
Compound 51
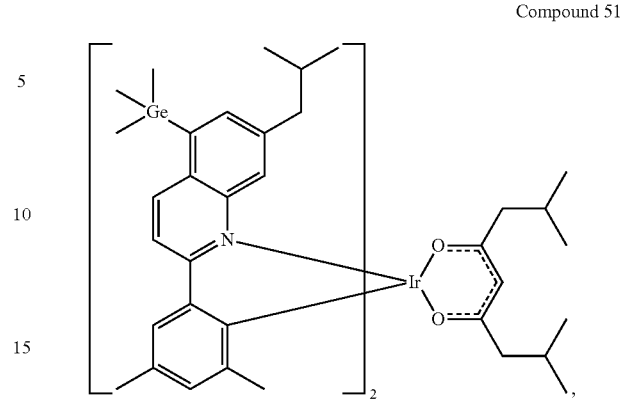
Compound 52
Compound 53
Compound 54
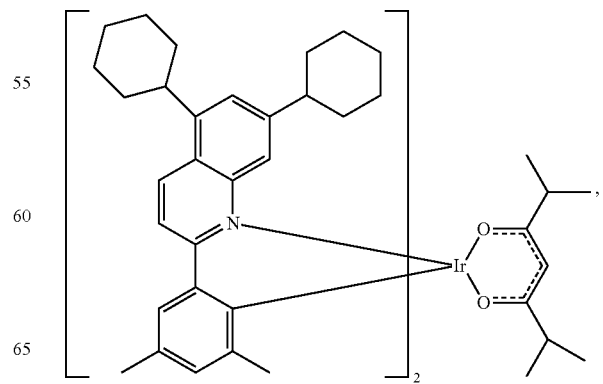

-continued

Compound 55

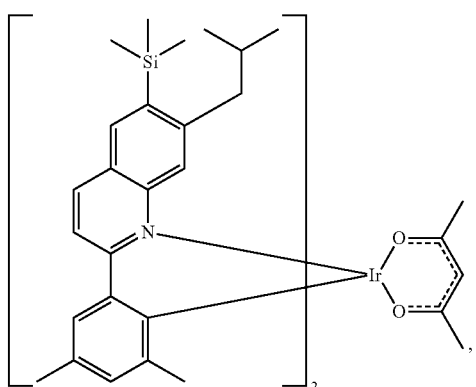

Compound 56

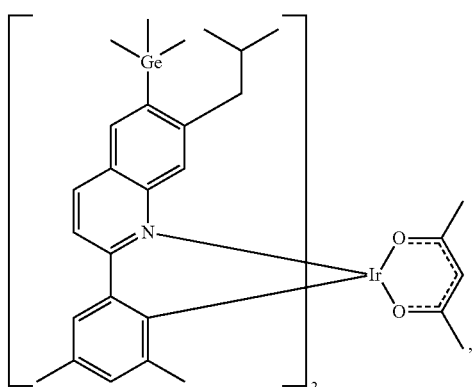

Compound 57

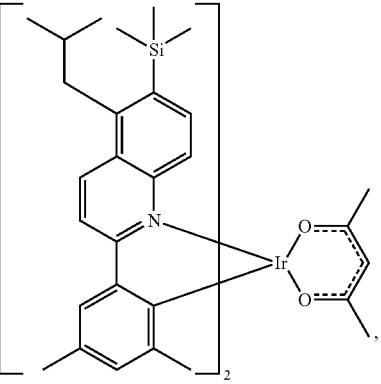

Compound 58

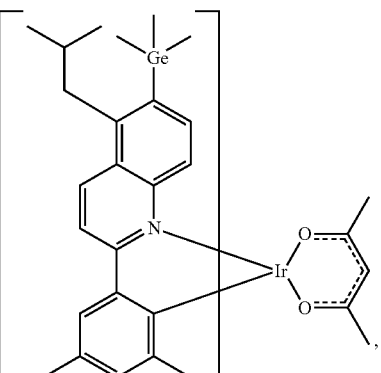

-continued

Compound 59

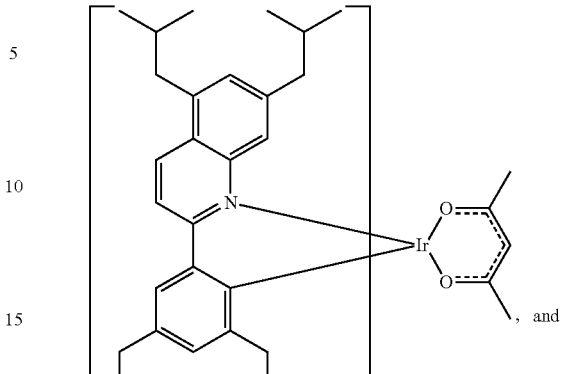
, and

Compound 60

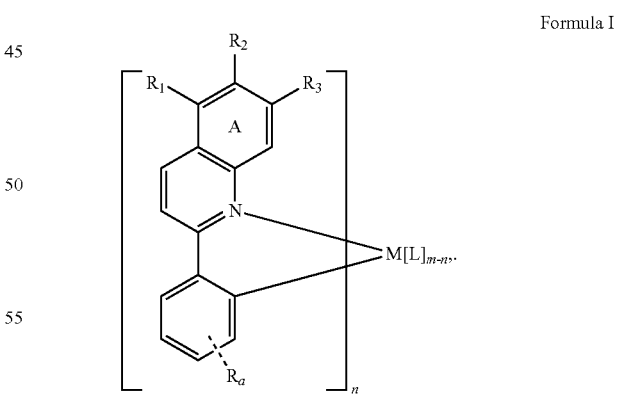
.

In one embodiment, a first device is provided. The first device comprises a first organic light emitting device, further comprising: an anode, a cathode, and an organic layer, disposed between the anode and the cathode, comprising a compound having the formula:

Formula I

M is a metal having an atomic weight higher than 40, L is a second ligand, m is the maximum coordination number of the metal M, and n is at least 1.

Each of $R_1$, $R_2$ and $R_3$ is independently selected from the group consisting of hydrogen, deuterium, alkyl, silyl, germyl, cycloalkyl, and combinations thereof. At least two of $R_1$, $R_2$ and $R_3$ are not hydrogen or deuterium. The sum of the number of carbon atoms in $R_1$, $R_2$ and $R_3$ is at least 4, and any carbon atom in $R_1$, $R_2$, or $R_3$ attached directly to ring A is a primary, a secondary, or a tertiary carbon atom. $R_a$ represents mono-, di-, tri-, or tetra-substitution, and $R_a$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the first device is a consumer product. In another embodiment, the first device is an organic light-emitting device.

In one embodiment, the first device comprises a lighting panel. In one embodiment, the organic layer is an emissive layer and the compound is a non-emissive dopant. In one embodiment, the organic layer further comprises a host.

In one embodiment, the host is a metal 8-hydroxyquinolate.

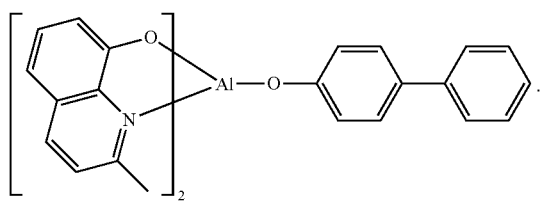

In one embodiment, the host is:

DEVICE EXAMPLES

All example devices were fabricated by high vacuum (<$10^{-7}$ Torr) thermal evaporation (VTE). The anode electrode is 1200 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound A as the hole injection layer (HIL), 400 Å of 4,4'-bis[N-(1-naphthyl)-N-phenylamino]biphenyl (NPD) as the hole transporting layer (HTL), 300 Å of the compound of Formula I doped in with BAlq as host with 4, 6, or 8 wt % of an iridium-containing phosphorescent compound as the emissive layer (EML), 450 or 550 Å of $Alq_3$ (tris-8-hydroxyquinoline aluminum) as the electron transport layer (ETL). Comparative Examples with Compound B, C, D, and E were fabricated similarly to the Device Examples except that the Compound B, C, D, and E were used as the emitters in the EML.

The device results and data are summarized in Tables 1 and 2 from those devices. As used herein, Compounds A, B, C, D and E have the following structures:

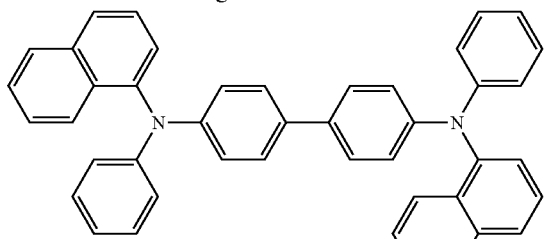

NPD

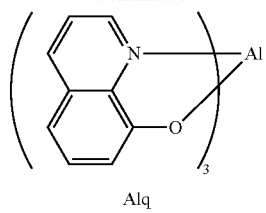

Alq

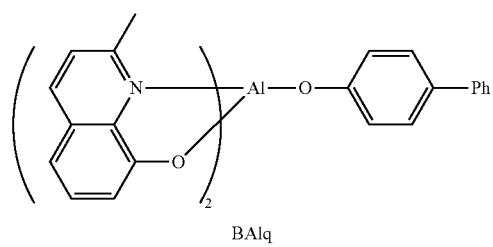

BAlq

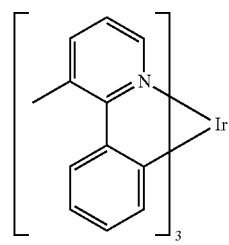

Compound A

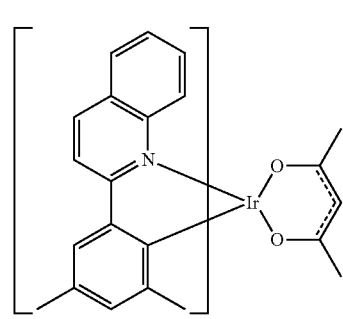

Compound B

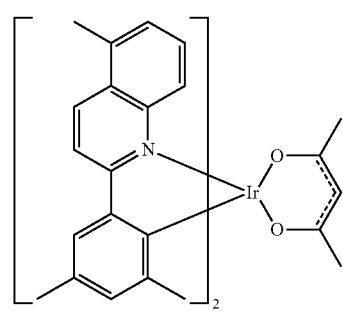

Compound C

-continued

Compound D

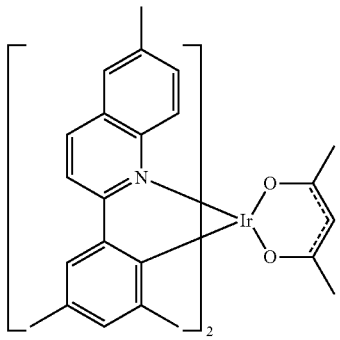

Compound E

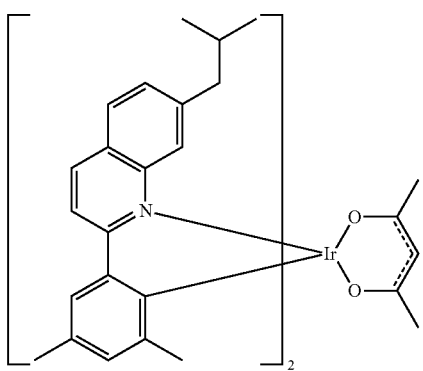

TABLE 1

Device structures of invention compounds and comparative compound

| Example | HIL | HTL | EML (300 Å, doping %) | | Blocking Layer | ETL |
|---|---|---|---|---|---|---|
| Comparative Example 1 | Compound A 100 Å | NPD 400 Å | BAlq | Compound B 4% | None | Alq 550 Å |
| Comparative Example 2 | Compound A 100 Å | NPD 400 Å | BAlq | Compound B 6% | None | Alq 550 Å |
| Comparative Example 3 | Compound A 100 Å | NPD 400 Å | BAlq | Compound B 8% | None | Alq 550 Å |
| Comparative Example 4 | Compound A 100 Å | NPD 400 Å | BAlq | Compound B 6% | BAlq 100 Å | Alq 450 Å |
| Comparative Example 5 | Compound A 100 Å | NPD 400 Å | BAlq | Compound C 6% | None | Alq 550 Å |
| Comparative Example 6 | Compound A 100 Å | NPD 400 Å | BAlq | Compound D 6% | None | Alq 550 Å |
| Comparative Example 7 | Compound A 100 Å | NPD 400 Å | BAlq | Compound E 6% | None | Alq 550 Å |
| Example 1 | Compound A 100 Å | NPD 400 Å | BAlq | Compound 1 4% | None | Alq 550 Å |
| Example 2 | Compound A 100 Å | NPD 400 Å | BAlq | Compound 1 6% | None | Alq 550 Å |
| Example 3 | Compound A 100 Å | NPD 400 Å | BAlq | Compound 1 8% | None | Alq 550 Å |
| Example 4 | Compound A 100 Å | NPD 400 Å | BAlq | Compound 1 6% | BAlq 100 Å | Alq 450 Å |
| Example 5 | Compound A 100 Å | NPD 400 Å | BAlq | Compound 2 4% | None | Alq 550 Å |
| Example 6 | Compound A 100 Å | NPD 400 Å | BAlq | Compound 2 6% | None | Alq 550 Å |

TABLE 1-continued

Device structures of invention compounds and comparative compound

| Example | HIL | HTL | EML (300 Å, doping %) | | Blocking Layer | ETL |
|---|---|---|---|---|---|---|
| Example 7 | Compound A 100 Å | NPD 400 Å | BAlq | Compound 2 8% | None | Alq 550 Å |
| Example 8 | Compound A 100 Å | NPD 400 Å | BAlq | Compound 2 6% | BAlq 100 Å | Alq 450 Å |

TABLE 2

VTE Device Results

| | x | y | $\lambda_{max}$ (nm) | FWHM (nm) | Voltage (V) | LE (Cd/A) | EQE (%) | PE (lm/W) | LT80% (h) |
|---|---|---|---|---|---|---|---|---|---|
| Comparative Example 1 Compound B | 0.665 | 0.332 | 620 | 62 | 9.2 | 19.6 | 17.8 | 6.7 | 410 |
| Comparative Example 2 Compound B | 0.667 | 0.330 | 622 | 62 | 9.0 | 19.1 | 18.2 | 6.7 | 404 |
| Comparative Example 3 Compound B | 0.668 | 0.329 | 622 | 64 | 8.5 | 17.9 | 17.4 | 6.6 | 490 |
| Comparative Example 4 Compound B | 0.667 | 0.330 | 622 | 62 | 9.6 | 19.3 | 18.2 | 6.3 | 400 |
| Comparative Example 5 Compound C | 0.662 | 0.336 | 619 | 64 | 8.2 | 20.9 | 18.4 | 8.0 | 274 |
| Comparative Example 6 Compound D | 0.656 | 0.342 | 616 | 65 | 9.1 | 22.1 | 18.1 | 7.63 | 375 |
| Comparative Example 7 Compound E | 0.652 | 0.345 | 614 | 58 | 8.5 | 25 | 18.8 | 9.2 | 160 |
| Example 1 Compound 1 | 0.650 | 0.347 | 612 | 62 | 8.7 | 26.1 | 20 | 9.4 | 114.6 |
| Example 2 Compound 1 | 0.653 | 0.344 | 614 | 60 | 8.2 | 28 | 21.7 | 10.6 | 148.0 |
| Example 3 Compound 1 | 0.653 | 0.343 | 614 | 60 | 7.6 | 28 | 22.1 | 11.5 | 138.8 |
| Example 4 Compound 1 | 0.653 | 0.344 | 614 | 60 | 8.6 | 28.7 | 22.3 | 10.4 | 108 |
| Example 5 Compound 2 | 0.642 | 0.355 | 608 | 54 | 8.7 | 32.3 | 21.6 | 11.6 | 38 |
| Example 6 Compound 2 | 0.646 | 0.351 | 610 | 56 | 8.4 | 31.3 | 21.9 | 11.7 | 26 |
| Example 7 Compound 2 | 0.648 | 0.349 | 612 | 56 | 7.9 | 30.3 | 21.8 | 12.1 | 10 |
| Example 8 Compound 2 | 0.646 | 0.351 | 612 | 54 | 8.9 | 31.2 | 21.9 | 11.0 | 18 |

Table 2 is a summary of the device data. The luminous efficiency (LE), external quantum efficiency (EQE) and power efficiency (PE) were measured at 1000 nits, while the lifetime ($LT_{80\%}$) was defined as the time required for the device to decay to 80% of its initial luminance under a constant current density of 40 mA/cm².

From Table 2, it can be seen that the EQE, LE and PE of compounds of Formula I are all greater, and hence superior, to the Comparative Compounds under the same device configuration. The comparison is based on the following compound pairs with the same device configuration, in each case the Example compound (a compound of Formula I) is superior to the Comparative Compound): Example 1 vs. Comparative Example 1, Example 2 vs. Comparative Examples 2, 5, 6, and 7, Example 3 vs. Comparative Example 3, Example 4 vs. Comparative Example 4, Example 5 vs. Comparative Example 1, Example 6 vs. Comparative Examples 2, 5, 6, and 7, Example 7 vs. Comparative Example 3, and Example 8 vs. Comparative Example 4. For example, comparative Compound B at doping concentrations of 4%, 6%, 8%, without hole blocking layer, had lower EQE, LE, and PE at all doping concentrations than Compound 1 and Compound 2. The EQE values of Comparative Compound B are in the range of 17.4 to 18.2%, which are all lower than Compound 1 and Compound 2, which have EQE's in the range of 20 to 22.3% using the same device structure. Thus, the di-alkyl substituted Compound 1 and Compound 2 are more efficient than Comparative Compound B. Similar trends were observed for compounds of Formula I in devices containing a hole blocking layer when compared with Comparative Compound B. Additionally, these trends were also found in the comparison of the EQE and LE of Compound 1 or Compound 2 with Comparative Compound C, D, and E, which only have single alkyl group on the quinoline, indicating that the di-substituted alkylation is surprisingly more efficient than the single substituted Comparative Compounds C, D, and E. The results indicate that multi-substituted alkyl groups can improve device performance such as EQE and LE.

TABLE 3

Comparison of Sublimation Tempature of Di-alkyl substituted Compound B

| Compounds | Sublimation Temperature (° C.) | Temperature Difference Relative to Compound B |
|---|---|---|
| Compound B | 193 | |
| Compound 1 | 158 | 35 |
| Compound 2 | 193 | 0 |

It can be seen that di-alkylation on the heteroaromatic ring in compounds of Formula I can decrease the sublimation temperature of complex as shown in Table 3. It was surprisingly discovered that di-alkyl substituted compounds of Formula I had lower sublimation temperatures than un-substituted compounds. For example, Compound 1 had a significantly lower sublimation temperature than Comparative Compound B (158° C. vs 193° C.) despite the fact that Compound 1 has a higher molecular weight than Comparative Compound B.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

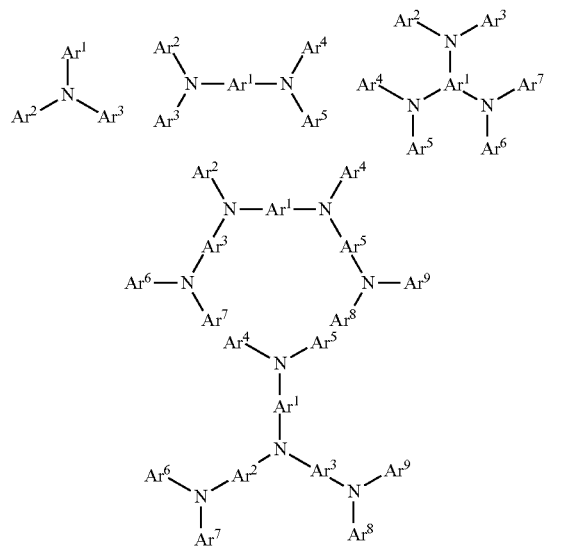

Each of Ar$^1$ to Ar$^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar$^1$ to Ar$^9$ is independently selected from the group consisting of:

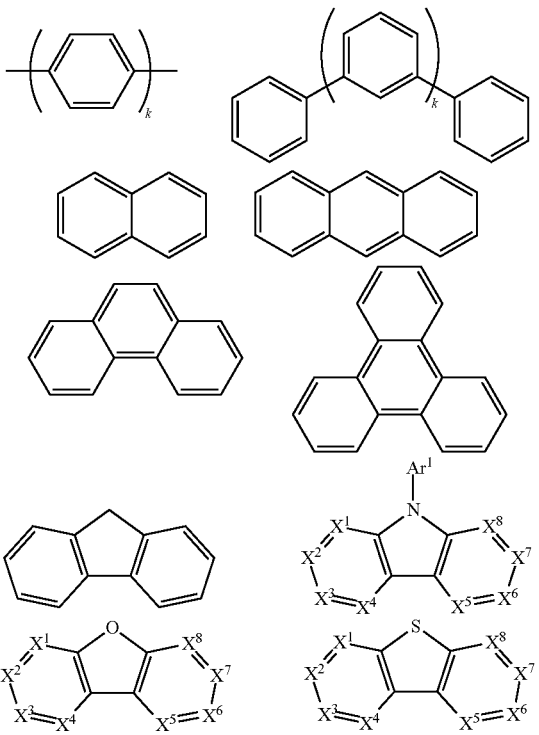

k is an integer from 1 to 20; X$^1$ to X$^8$ is C (including CH) or N; Ar$^1$ has the same group defined above.

Examples of metal complexes used in HIL or HTL include, but not limit to the following general formula:

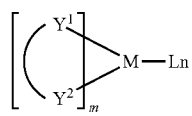

M is a metal, having an atomic weight greater than 40; (Y$^1$—Y$^2$) is a bidentate ligand, Y$^1$ and Y$^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, (Y$^1$—Y$^2$) is a 2-phenylpyridine derivative.

In another aspect, (Y$^1$—Y$^2$) is a carbene ligand.

In another aspect, M is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

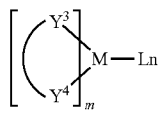

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

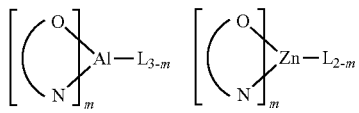

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

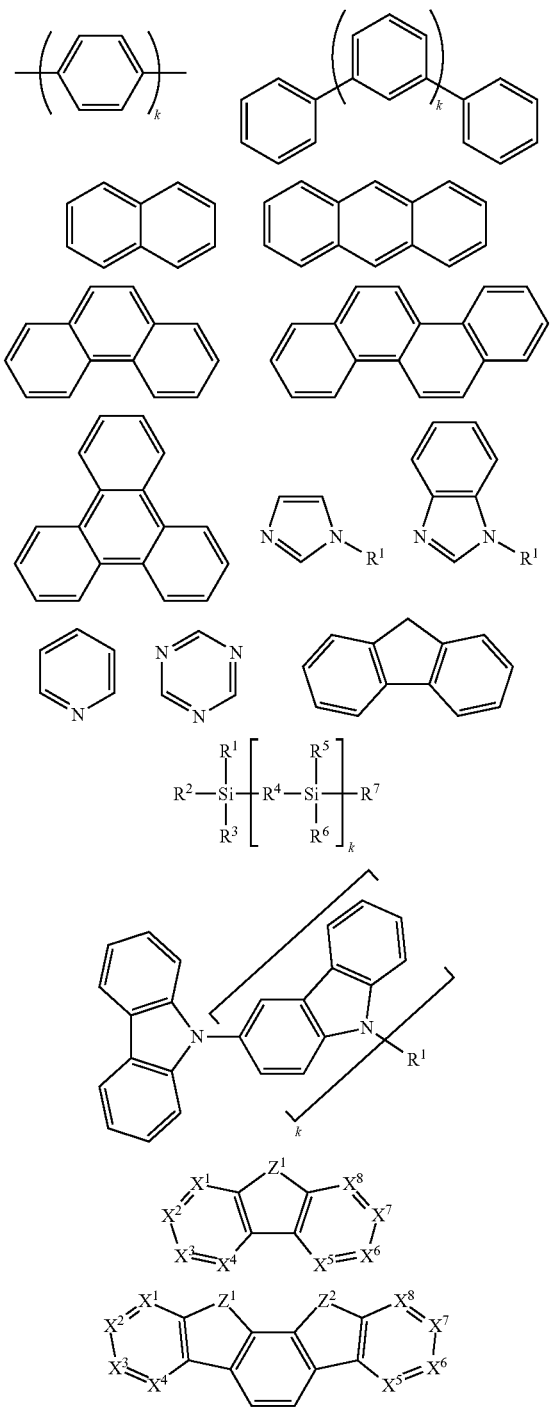

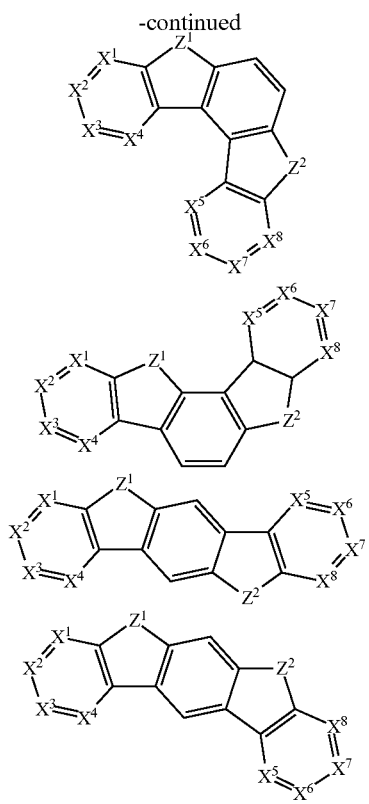

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

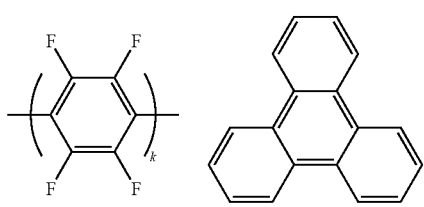

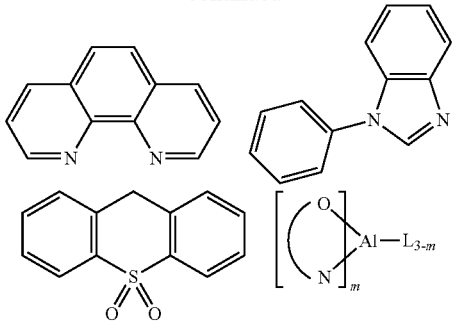

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

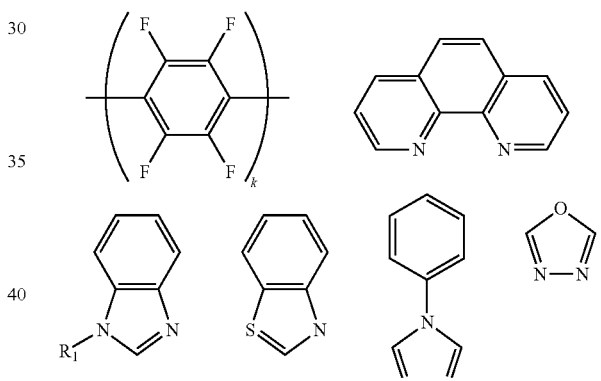

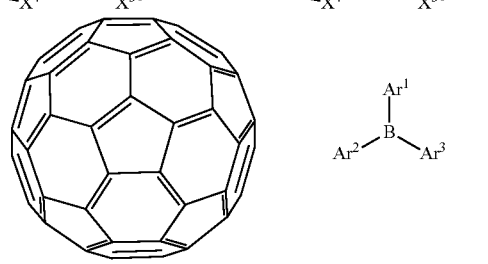

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

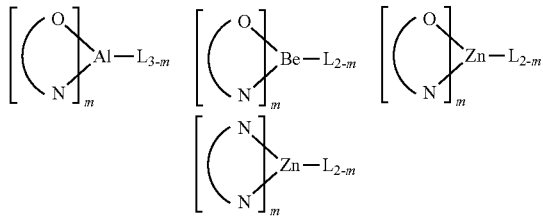

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially, or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
|---|---|---|
| Hole injection materials | | |
| Phthalocyanine and porphryin compounds | 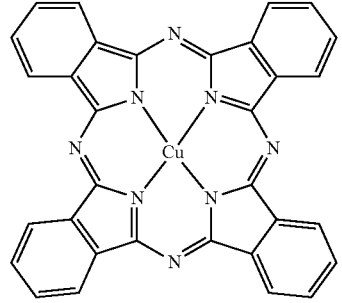 | Appl. Phys. Lett. 69, 2160 (1996) |
| Starburst triarylamines | 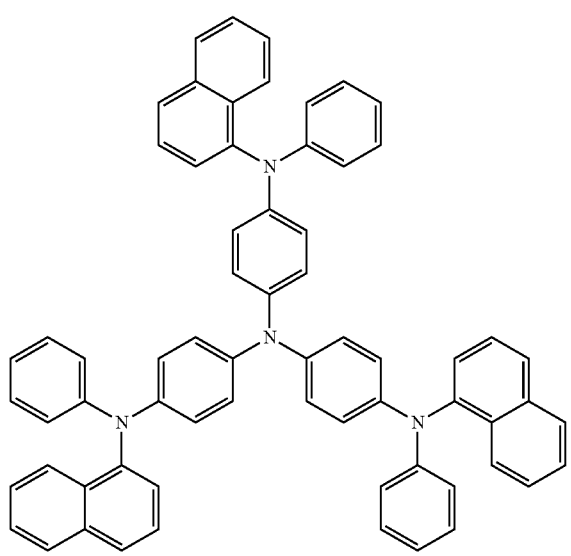 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | 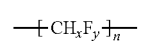 | Appl. Phys. Lett. 78, 673 (2001) |

TABLE 4-continued
| MATERIAL | EXAMPLES OF MATERIAL | PUBLICATIONS |
|---|---|---|
| Conducting polymers (e.g., PEDOT:PSS, polyaniline, polythiophene) | 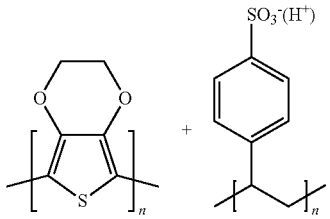 | Synth. Met. 87, 171 (1997) WO2007002683 |
| Phosphonic acid and sliane SAMs | 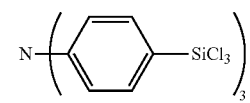 | US20030162053 |
| Triarylamine or polythiophene polymers with conductivity dopants | 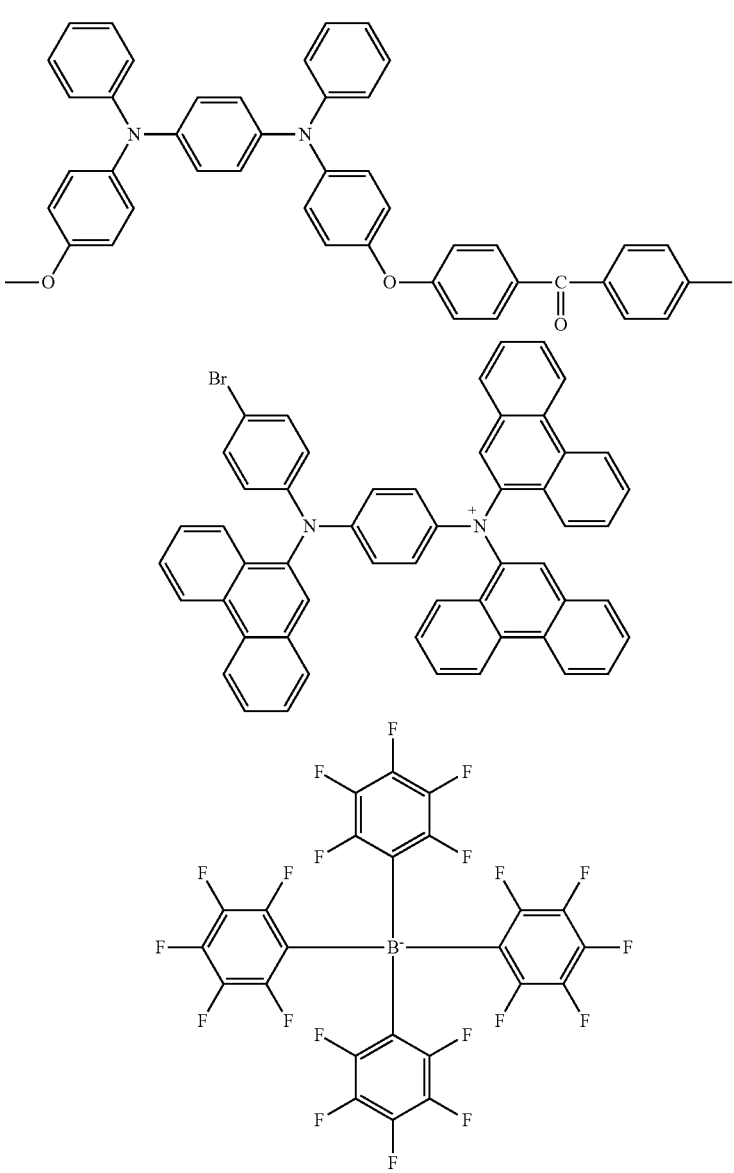 | EP1725079A1 |

TABLE 4-continued

| MATERIAL | EXAMPLES OF MATERIAL | PUBLICATIONS |
| --- | --- | --- |
| Organic compounds with conductive inorganic compounds, such as molybdenum and tungsten oxides | [chemical structure] + MoO$_x$ | US20050123751<br>SID Symposium Digest, 37, 923 (2006)<br>WO2009018009 |
| n-type semiconducting organic complexes | [chemical structure] | US20020158242 |
| Metal organometallic complexes | [chemical structure] | US20060240279 |
| Cross-linkable compounds | [chemical structure] | US20080220265 |

TABLE 4-continued

| MATERIAL | EXAMPLES OF MATERIAL | PUBLICATIONS |
| --- | --- | --- |
| Polythiophene based polymers and copolymers | | WO 2011075644<br>EP2350216 |

Hole transporting materials

| | | |
| --- | --- | --- |
| Triarylamines (e.g., TPD, α-NPD) | | Appl. Phys. Lett. 51, 913 (1987) |
| | | U.S. Pat. No. 5,061,569 |
| | | EP650955 |

TABLE 4-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |

| MATERIAL | EXAMPLES OF MATERIAL | PUBLICATIONS |
|---|---|---|
| Arylamine carbazole compounds | 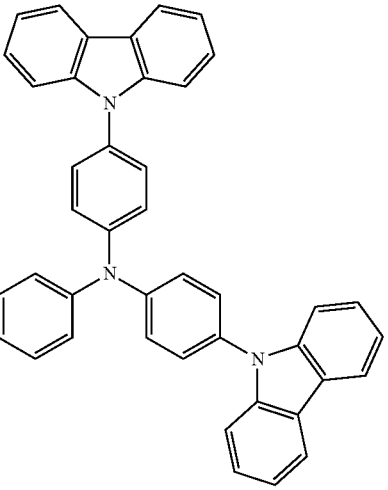 | Adv. Mater. 6, 677 (1994), US20080124572 |
| Triarylamine with (di)benzothiophene/ (di)benzofuran | 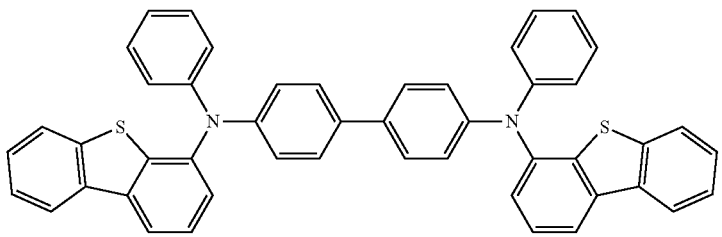 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 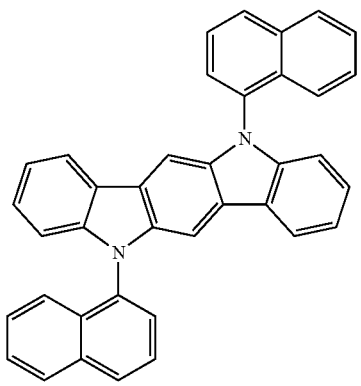 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 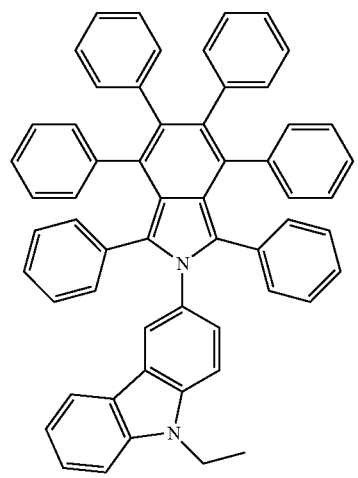 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |

TABLE 4-continued

| MATERIAL | EXAMPLES OF MATERIAL | PUBLICATIONS |
| --- | --- | --- |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |

TABLE 4-continued

| MATERIAL | EXAMPLES OF MATERIAL | PUBLICATIONS |
| --- | --- | --- |
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| Arylcarbazoles | | Appl. Phys. Lett. 78, 1622 (2001) |
| --- | --- | --- |

TABLE 4-continued
| MATERIAL | EXAMPLES OF MATERIAL | PUBLICATIONS |
|---|---|---|
| | 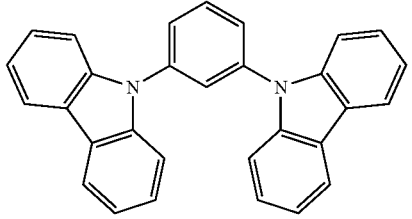 [SMILES: c1cc(-n2c3ccccc3c3ccccc32)cc(-n2c3ccccc3c3ccccc32)c1] | US20030175553 |
| | 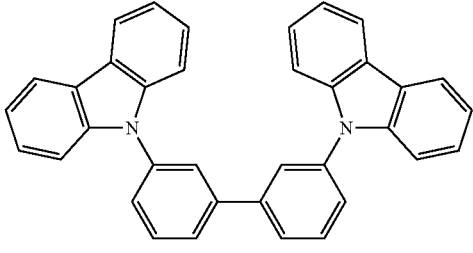 [SMILES: c1cc(-c2cccc(-n3c4ccccc4c4ccccc43)c2)cc(-n2c3ccccc3c3ccccc32)c1] | WO2001039234 |
| Aryltriphenylene compounds | 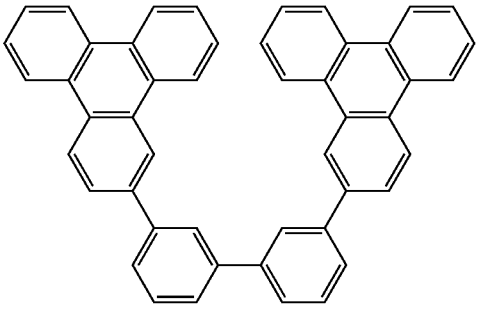 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 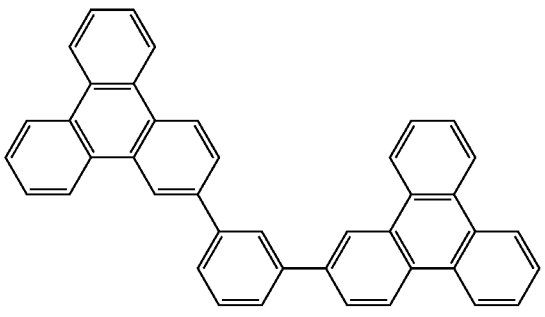 [SMILES: c1cc(-c2ccc3c4ccccc4c4ccccc4c3c2)cc(-c2ccc3c4ccccc4c4ccccc4c3c2)c1] | US20060280965 |
| | 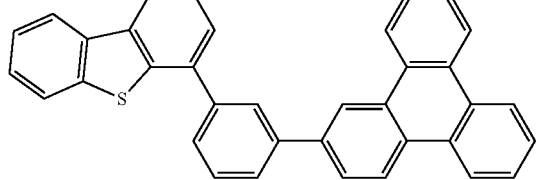 | WO2009021126 |

TABLE 4-continued
| MATERIAL | EXAMPLES OF MATERIAL | PUBLICATIONS |
| --- | --- | --- |
| Poly-fused heteroaryl compounds | 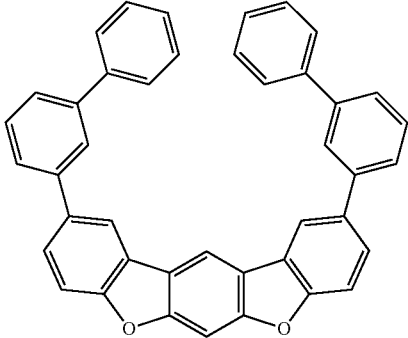 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 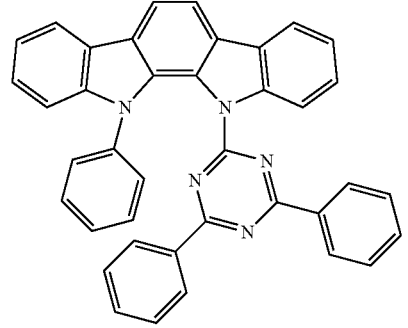 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 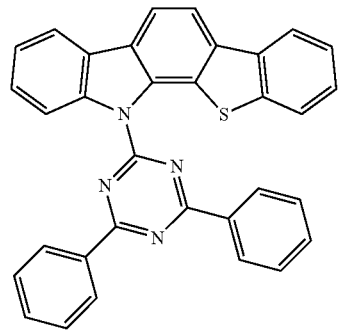 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 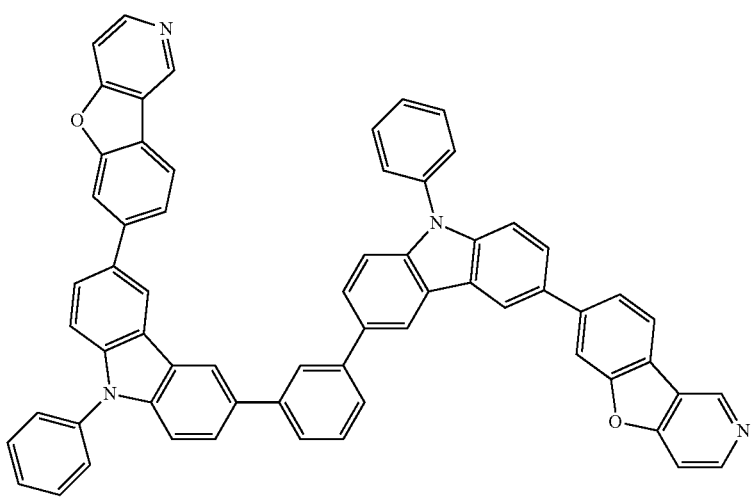 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 4-continued
| MATERIAL | EXAMPLES OF MATERIAL | PUBLICATIONS |
|---|---|---|
| | 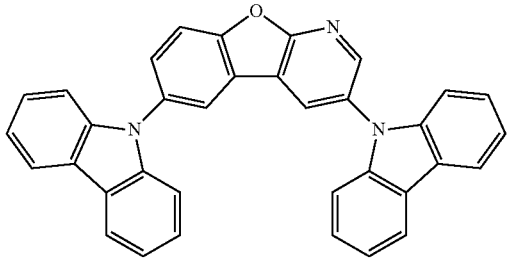 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 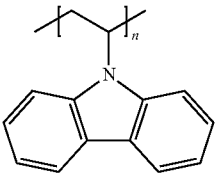 | Appl. Phys. Lett. 77, 2280 (2000) |
| Spirofluorene compounds | 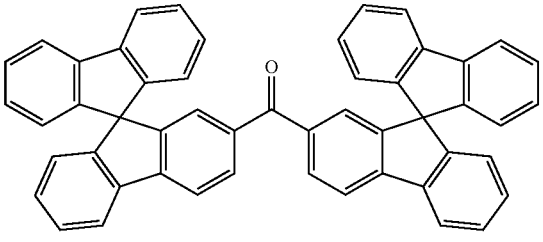 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 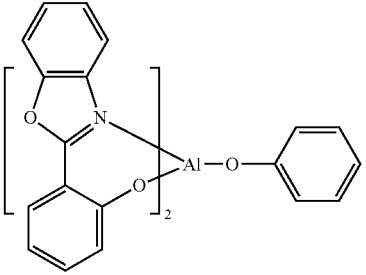 | WO2005089025 |
| | 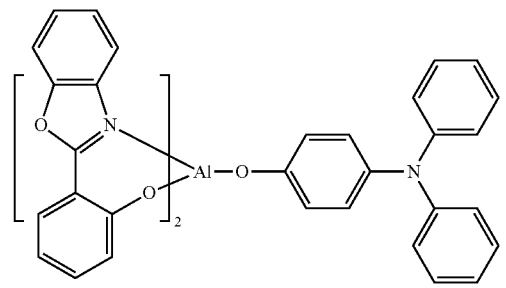 | WO2006132173 |
| | 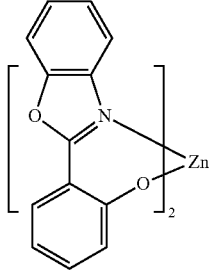 | JP200511610 |

TABLE 4-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |

TABLE 4-continued

| MATERIAL | EXAMPLES OF MATERIAL | PUBLICATIONS |
| --- | --- | --- |
| | | WO2004107822 |
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

Blue hosts

| Arylcarbazoles | | Appl. Phys. Lett, 82, 2422 (2003) |
| --- | --- | --- |

| MATERIAL | EXAMPLES OF MATERIAL | PUBLICATIONS |
|---|---|---|
| | 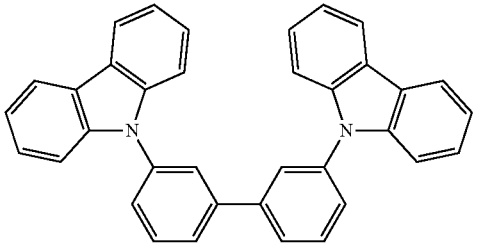 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran- carbazole compounds | 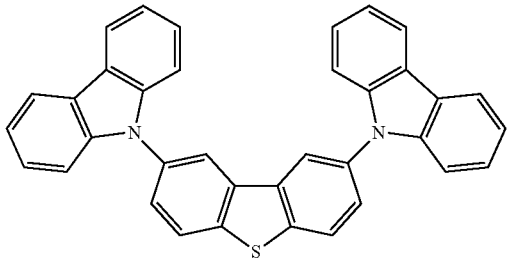 [SMILES: c1ccc2c(c1)c1ccccc1n2-c1ccc2sc3ccc(-n4c5ccccc5c5ccccc54)cc3c2c1] | WO2006114966, US20090167162 |
| | 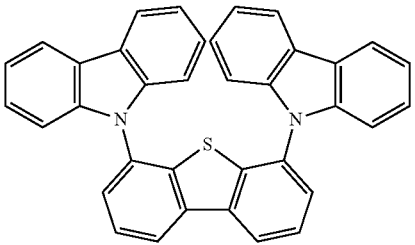 [SMILES: c1cc(-n2c3ccccc3c3ccccc32)c2sc3c(-n4c5ccccc5c5ccccc54)cccc3c2c1] | US20090167162 |
| | 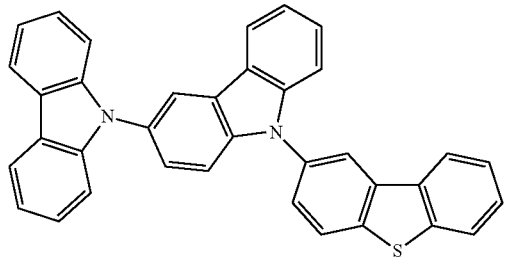 [SMILES: c1ccc2c(c1)sc1ccc(-n3c4ccccc4c4cc(-n5c6ccccc6c6ccccc65)ccc43)cc12] | WO2009086028 |
| | 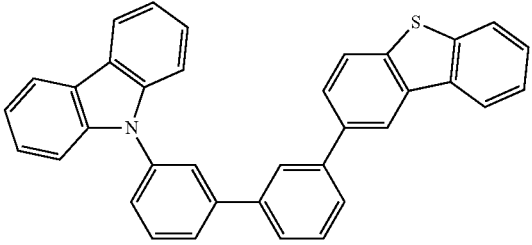 [SMILES: c1cc(-c2cccc(-n3c4ccccc4c4ccccc43)c2)cc(-c2ccc3sc4ccccc4c3c2)c1] | US20090030202, US20090017330 |
| | 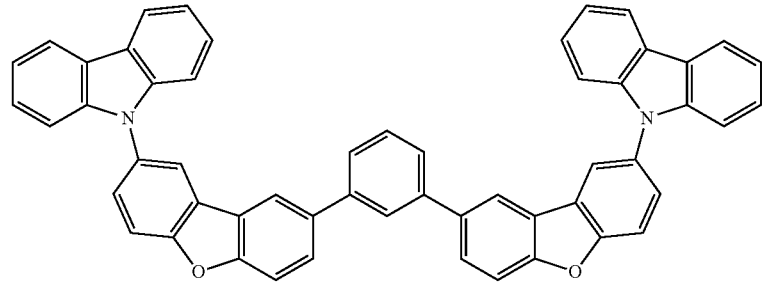 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |

TABLE 4-continued
| MATERIAL | EXAMPLES OF MATERIAL | PUBLICATIONS |
|---|---|---|
| Silicon aryl compounds | 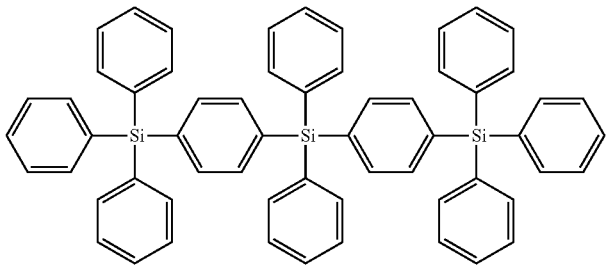 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 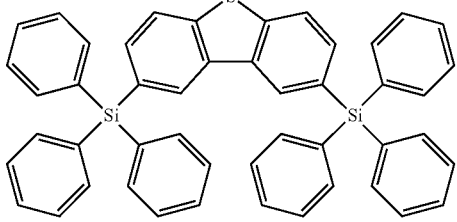 | WO2009003898 |
| Silicon/Germanium aryl compounds | 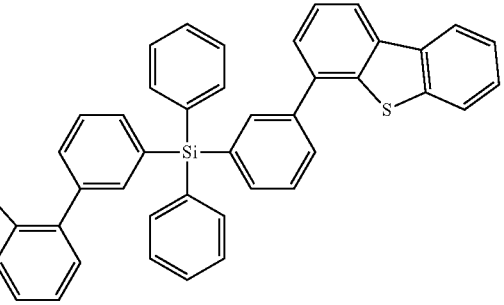 | EP2034538A |
| Aryl benzoyl ester | 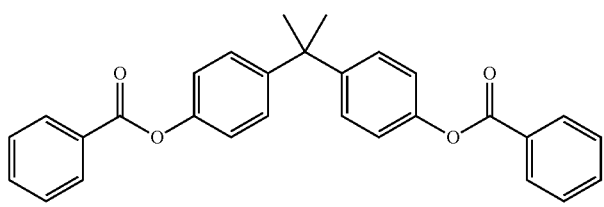 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 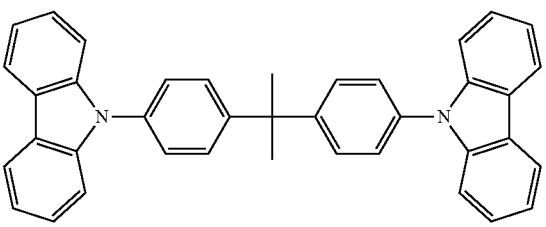 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 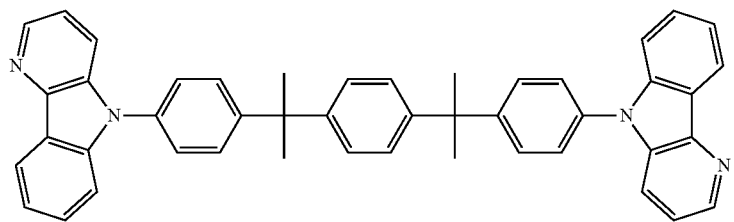 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 4-continued

| MATERIAL | EXAMPLES OF MATERIAL | PUBLICATIONS |
| --- | --- | --- |
| High triplet metal organometallic complex | | U.S. Pat. No. 7,154,114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

TABLE 4-continued

| MATERIAL | EXAMPLES OF MATERIAL | PUBLICATIONS |
|---|---|---|
| | | US20060202194 |
| | | US20060202194 |
| | | US20070087321 |
| | | US20080261076<br>US20100090591 |
| | | US20070087321 |

| MATERIAL | EXAMPLES OF MATERIAL | PUBLICATIONS |
|---|---|---|
| | 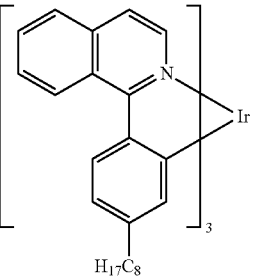 | Adv. Mater. 19, 739 (2007) |
| | 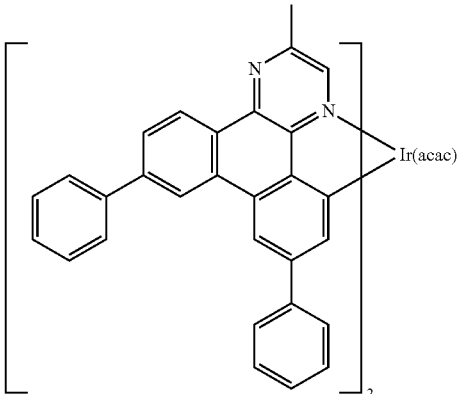 | WO2009100991 |
| | 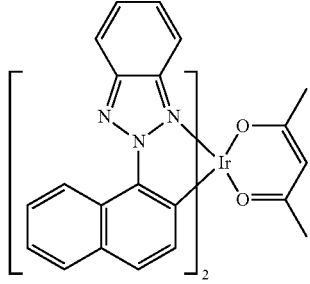 | WO2008101842 |
| | 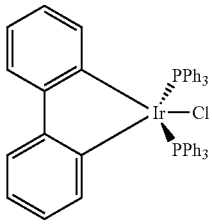 | U.S. Pat. No. 7,232,618 |
| Platinum(II) organometallic complexes | 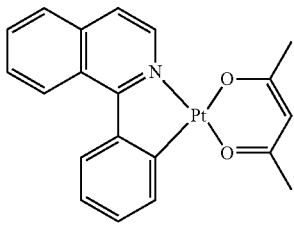 | WO2003040257 |

TABLE 4-continued
| MATERIAL | EXAMPLES OF MATERIAL | PUBLICATIONS |
|---|---|---|
| | 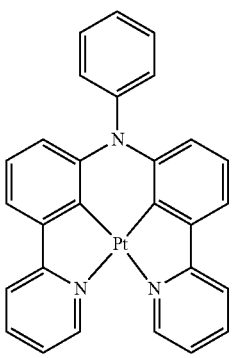 | US20070103060 |
| Osminum(III) complexes | 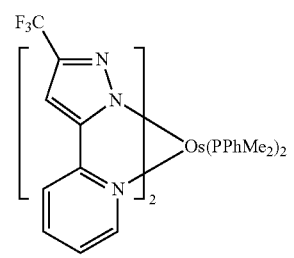 | Chem. Mater. 17, 3532 (2005) |
| Ruthenium(II) complexes | 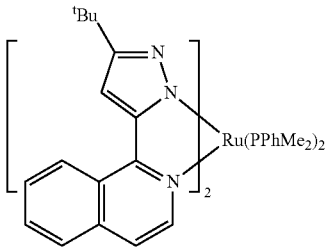 | Adv. Mater. 17, 1059 (2005) |
| Rhenium (I), (II), and (III) complexes | 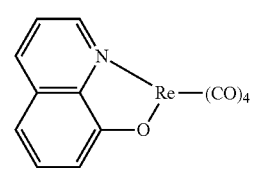 | US20050244673 |
Green dopants
| | | |
|---|---|---|
| Iridium(III) organometallic complexes | 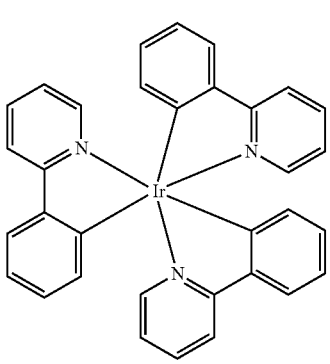
and its derivatives | Inorg. Chem. 40, 1704 (2001) |

TABLE 4-continued
| MATERIAL | EXAMPLES OF MATERIAL | PUBLICATIONS |
|---|---|---|
| | 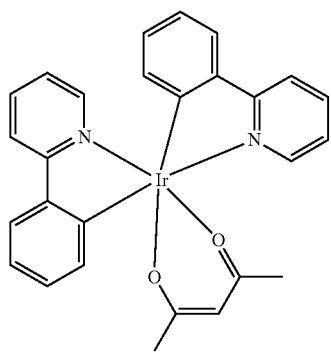 | US20020034656 |
| | 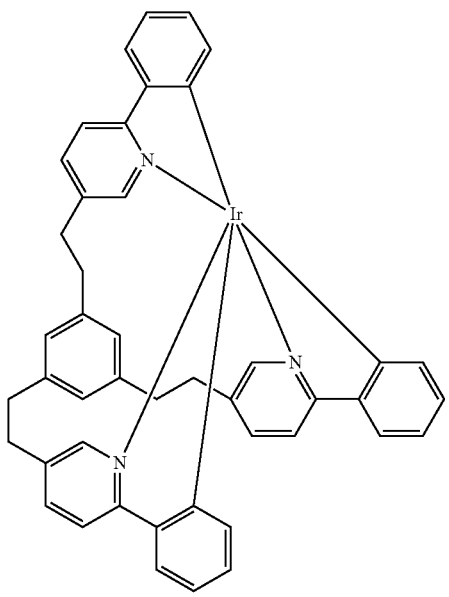 | U.S. Pat. No. 7,332,232 |
| | 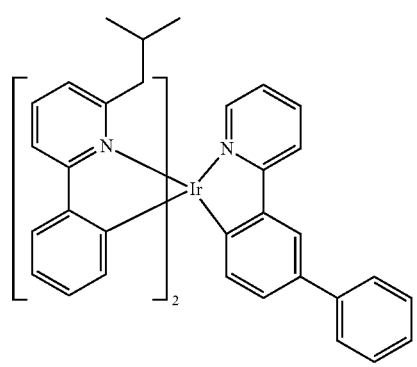 | US20090108737 |

TABLE 4-continued

| MATERIAL | EXAMPLES OF MATERIAL | PUBLICATIONS |
|---|---|---|
| | | WO2010028151 |
| | | EP1841834B |
| | | US20060127696 |
| | | US20090039776 |
| | | U.S. Pat. No. 6,921,915 |

TABLE 4-continued

| MATERIAL | EXAMPLES OF MATERIAL | PUBLICATIONS |
|---|---|---|
| | | US20100244004 |
| | | U.S. Pat. No. 6,687,266 |
| | | Chem. Mater. 16, 2480 (2004) |
| | | US20070190359 |
| | | US 20060008670 JP2007123392 |

| MATERIAL | EXAMPLES OF MATERIAL | PUBLICATIONS |
|---|---|---|
| | | WO2010086089, WO2011044988 |
| | | Adv. Mater. 16, 2003 (2004) |
| | | Angew. Chem. Int. Ed. 2006, 45, 7800 |
| | | WO2009050290 |
| | | US20090165846 |
| | | US20080015355 |

TABLE 4-continued

| MATERIAL | EXAMPLES OF MATERIAL | PUBLICATIONS |
|---|---|---|
| | [Ir(bpy)₃](PF₆)₃ complex structure | US20010015432 |
| | Ir complex with B-bridged bipyridine ligand | US20100295032 |
| Monomer for polymeric metal organometallic compounds | Ir complex with phenylpyridine and styryl-acetylacetonate ligands | U.S. Pat. No. 7,250,226, U.S. Pat. No. 7,396,598 |
| Pt(II) organometallic complexes, including polydentated ligands | Pt–Cl complex with N^C^N tridentate ligand | Appl. Phys. Lett. 86, 153505 (2005) |
| | Pt–O(phenoxide) complex with N^C^N tridentate ligand | Appl. Phys. Lett. 86, 153505 (2005) |

TABLE 4-continued

| MATERIAL | EXAMPLES OF MATERIAL | PUBLICATIONS |
|---|---|---|
| | | Chem. Lett. 34, 592 (2005) |
| | | WO2002015645 |
| | | US20060263635 |
| | | US20060182992<br>US20070103060 |

TABLE 4-continued

| MATERIAL | EXAMPLES OF MATERIAL | PUBLICATIONS |
| --- | --- | --- |
| Cu complexes | | WO2009000673 |
| | | US20070111026 |
| Gold complexes | | Chem. Commun. 2906 (2005) |
| Rhenium(III) complexes | | Inorg. Chem. 42, 1248 (2003) |

TABLE 4-continued

| MATERIAL | EXAMPLES OF MATERIAL | PUBLICATIONS |
| --- | --- | --- |
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE 4-continued
| MATERIAL | EXAMPLES OF MATERIAL | PUBLICATIONS |
|---|---|---|
| Blue dopants | | |
| Iridium(III) organometallic complexes | 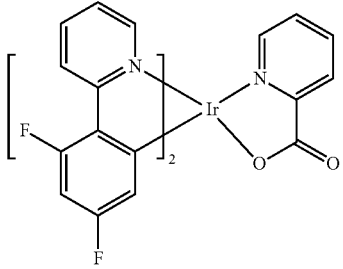 | WO2002002714 |
| | 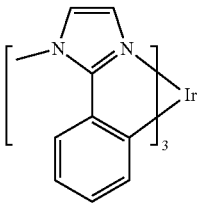 | WO2006009024 |
| | 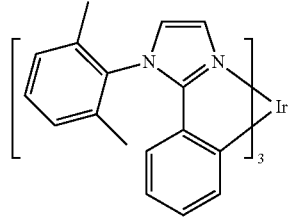 | US20060251923<br>US20110057559<br>US20110204333 |
| | 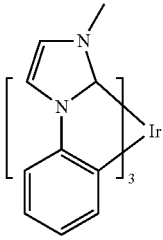 | U.S. Pat. No. 7,393,599,<br>WO2006056418,<br>US20050260441,<br>WO2005019373 |
| | 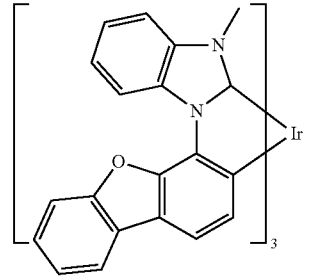 | U.S. Pat. No. 7,534,505 |
| | 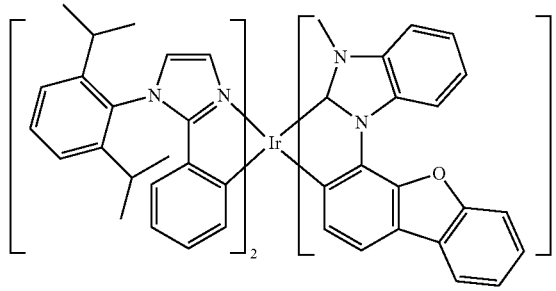 | WO2011051404 |

TABLE 4-continued

| MATERIAL | EXAMPLES OF MATERIAL | PUBLICATIONS |
|---|---|---|
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 1 (2008) |

| MATERIAL | EXAMPLES OF MATERIAL | PUBLICATIONS |
|---|---|---|
| | 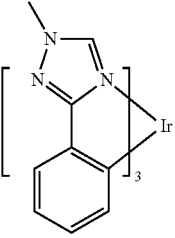 | Chem. Mater. 18, 5119 (2006) |
| | 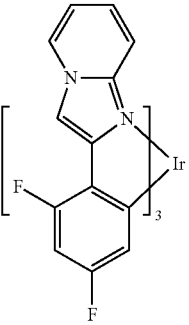 | Inorg. Chem. 46, 4308 (2007) |
| | 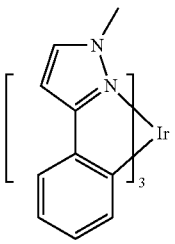 | WO2005123873 |
| | 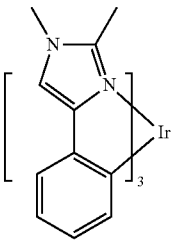 | WO2005123873 |
| | 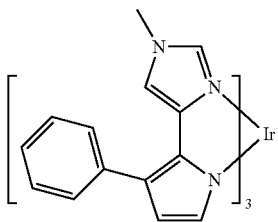 | WO2007004380 |

TABLE 4-continued

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 4-continued

| MATERIAL | EXAMPLES OF MATERIAL | PUBLICATIONS |
|---|---|---|
| Pt tetradentate complexes with at least one metal-carbene bond | 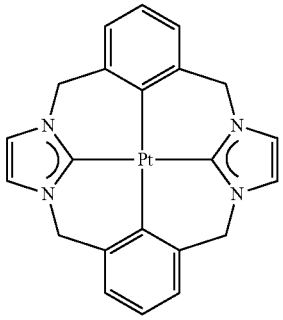 | U.S. Pat. No. 7,655,323 |

Exciton/hole blocking layer materials

| MATERIAL | EXAMPLES OF MATERIAL | PUBLICATIONS |
|---|---|---|
| Bathocuprine compounds (e.g., BCP, BPhen) | 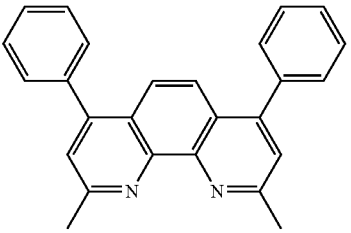 [SMILES: Cc1cc(-c2ccccc2)c2ccc3c(-c4ccccc4)cc(C)nc3c2n1] | Appl. Phys. Lett. 75, 4 (1999) |
| | 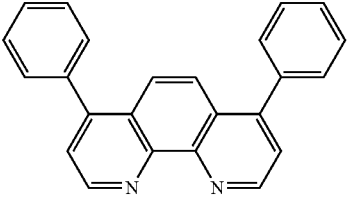 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 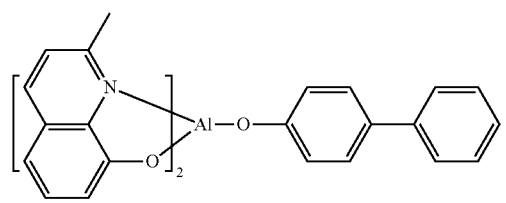 | Appl. Phys. Lett. 81, 162 (2002) |
| 5-member ring electron deficient heterocycles such as triazole, oxadiazole, imidazole, benzoimidazole | 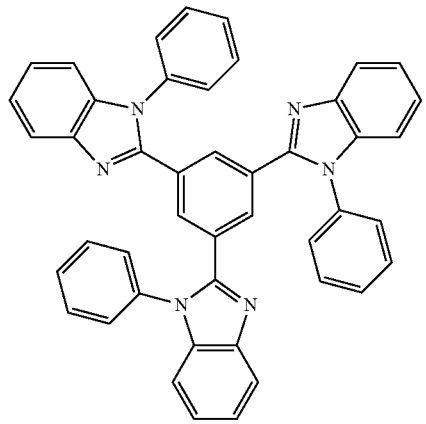 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 4-continued
| MATERIAL | EXAMPLES OF MATERIAL | PUBLICATIONS |
|---|---|---|
| Triphenylene compounds | 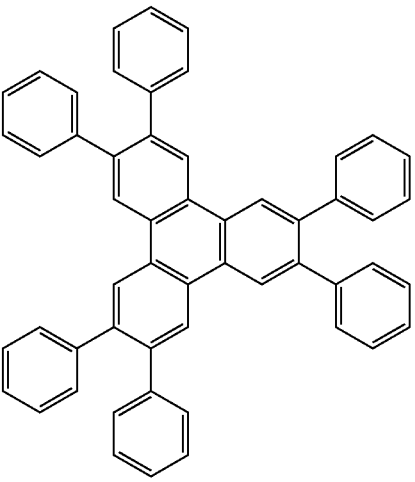 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 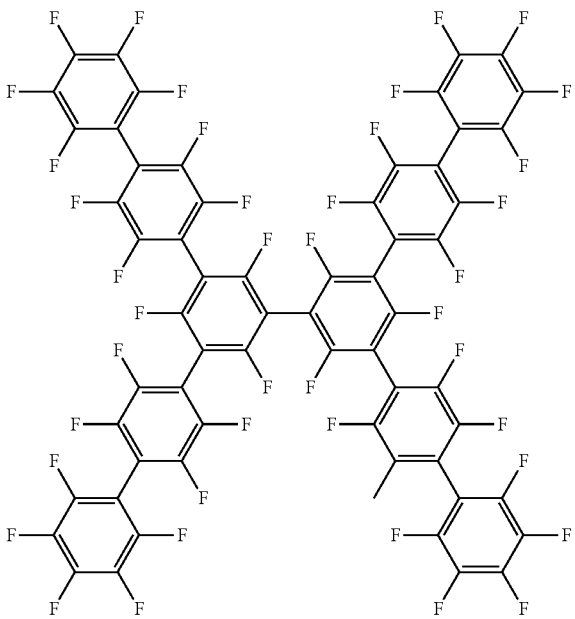 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 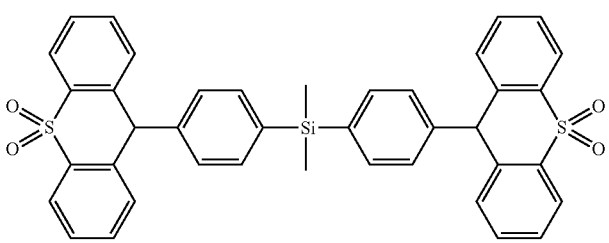 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 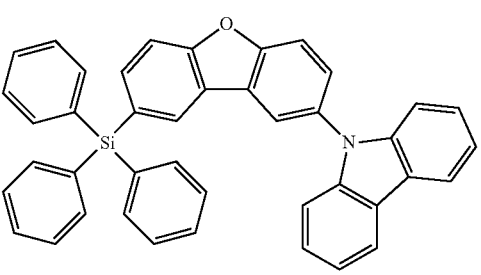 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 4-continued
| MATERIAL | EXAMPLES OF MATERIAL | PUBLICATIONS |
|---|---|---|
| Aza-carbazoles | 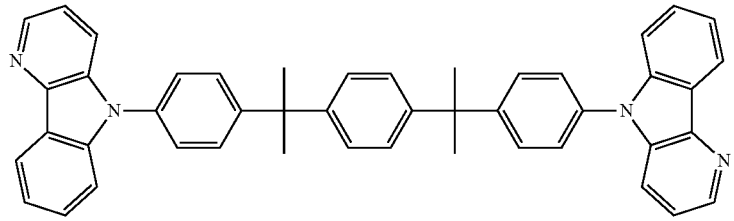 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials
| MATERIAL | EXAMPLES OF MATERIAL | PUBLICATIONS |
|---|---|---|
| Anthracene-benzoimidazole compounds | 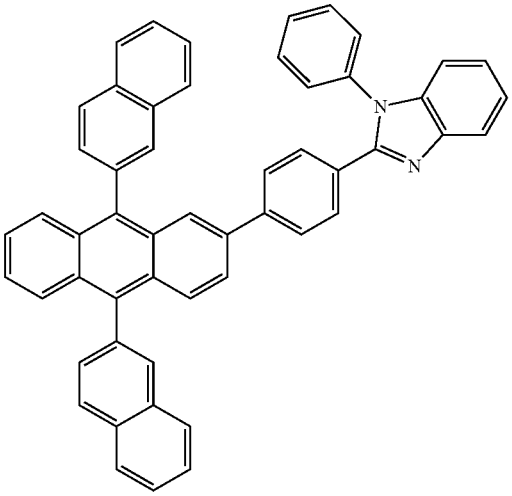 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 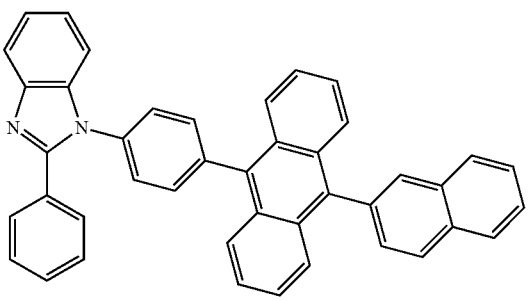 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 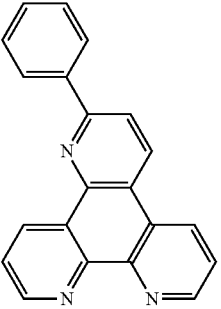 [SMILES: c1ccc(-c2ccc3c4cccnc4c4ncccc4c3n2)cc1] | US20090115316 |

TABLE 4-continued

| MATERIAL | EXAMPLES OF MATERIAL | PUBLICATIONS |
|---|---|---|
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 4-continued
| MATERIAL | EXAMPLES OF MATERIAL | PUBLICATIONS |
|---|---|---|
| | 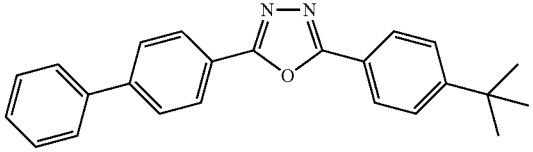 [SMILES: CC(C)(C)c1ccc(-c2nnc(-c3ccc(-c4ccccc4)cc3)o2)cc1] | Appl. Phys. Lett. 55, 1489 (1989) |
| | 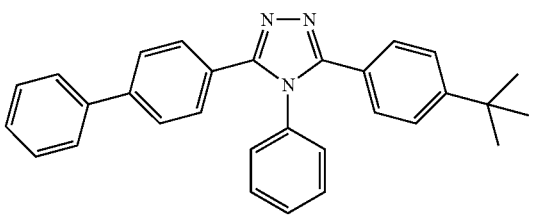 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 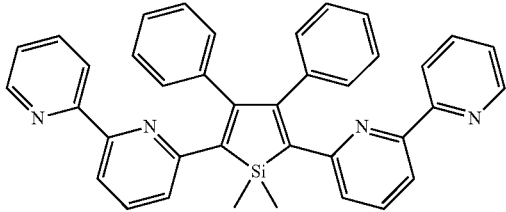 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 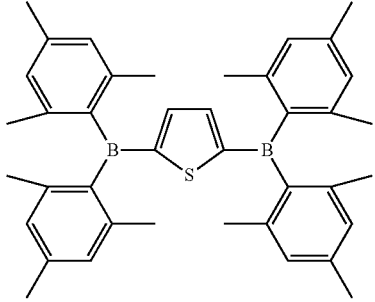 | J. Am. Chem. Soc. 120, 9714 (1998) |
| Fluorinated aromatic compounds | 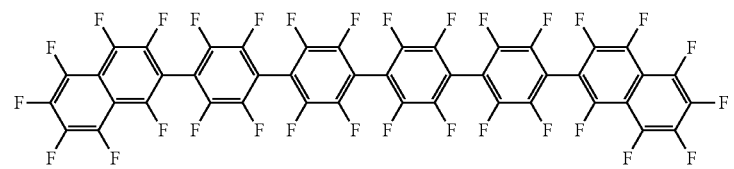 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 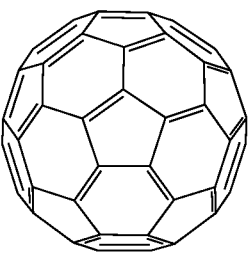 [SMILES: c1cc2c3ccc4c5ccc6c7ccc8c9ccc%10c1c1c2c2c3c4c3c5c6c4c7c8c5c9c%10c1c1c2c3c4c51] | US20090101870 |

TABLE 4-continued

| MATERIAL | EXAMPLES OF MATERIAL | PUBLICATIONS |
|---|---|---|
| Triazine complexes | | US20040036077 |
| Zn (N^N) complexes | | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DCM is dichloromethane, DMF is dimethylformamide, S-Phos is dicyclohexyl(2',6'-dimethoxy-[1,1'-biphenyl]-2-yl)phosphine.

Synthesis of Compound 1

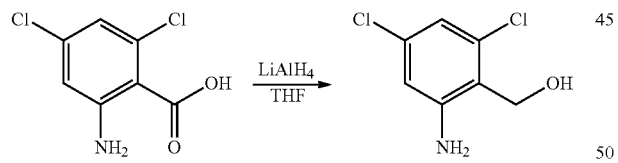

Synthesis of (2-amino-4,6-dichlorophenyl)methanol 2-amino-4,6-dichlorobenzoic acid (10.0 g, 48.5 mmol) was dissolved in 50 mL of anhydrous THF in a 250 mL 2 neck round bottom flask. The solution was cooled in an ice-water bath. A solution of lithium aluminum hydride (LAH) (40 mL, 2.0 M) in THF was then added dropwise. After all of the LAH was added, the reaction mixture was allowed to warm up to room temperature and stirred at room temperature for overnight. Water (5.1 mL) was added to the reaction mixture followed by 5.1 mL of 15% NaOH and then an additional 9.2 mL of water. The salts were filtered off and washed with THF. The filtrate was concentrated to give (2-amino-4,6-dichlorophenyl)methanol (11.1 g, wet) as a yellow solid, which was taken on to the next step without further purification.

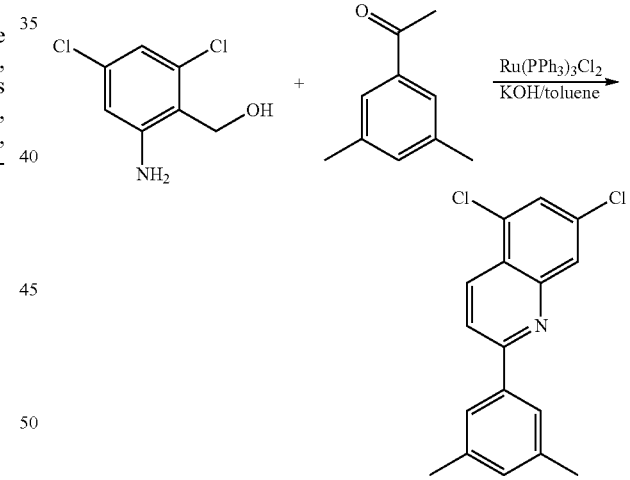

Synthesis of 5,7-dichloro-2-(3,5-dimethylphenyl)quinoline (2-amino-4,6-dichlorophenyl)methanol (11.1 g, 48.5 mmol), 3,5-dimethylacetophenone (11.1 g, 74.9 mmol), RuCl$_2$(PPh$_3$)$_3$ (0.25 g, 0.29 mmol), KOH (2.19 g, 39 mmol) was refluxed in 200 mL of toluene for 18 hours. Water was collected during the reaction using a Dean-Stark trap. The reaction mixture was allowed to cool to room temperature and filtered through a silica gel plug and eluted with DCM. The product after evaporation of solvent was further purified by Kugelrohr distillation and recrystallization from dichloromethane/iso-propanol to give 5,7-dichloro-2-(3,5-dimethylphenyl)quinolone (8.85 g, 60.3% yield).

romethane. The product was purified by column chromatography (4:1 to 1:1 hexanes/ethyl acetate, v/v) to give 5.2 g (41% yield) of 2-(3,5-dimethylphenyl)-5,7-diisobutylquinoline, which was confirmed by GCMS.

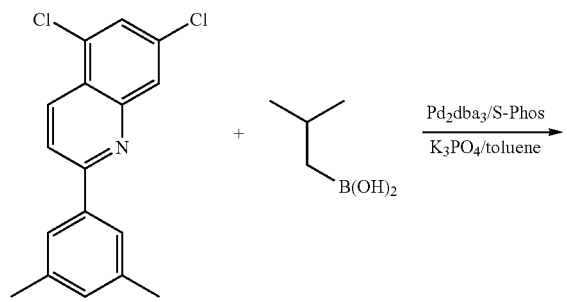

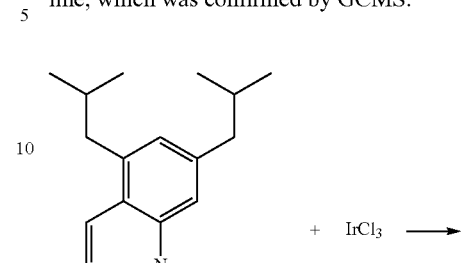

Synthesis of 2-(3,5-dimethylphenyl)-5,7-diisobutylquinoline 5,7-dichloro-2-(3,5-dimethylphenyl)quinoline (4.8 g, 15.9 mmol), isobutylboronic acid (6.48 g, 63.5 mmol), dicyclohexyl(2',6'-dimethoxy-[1,1'-biphenyl]-2-yl)phosphine (1.04 g, 2.54 mmol), $Pd_2(dba)_3$ (0.582 g, 0.635 mmol), potassium phosphate monohydrate (36.6 g, 159 mmol) and 2 mL of water were mixed in 240 mL of toluene. The system was degassed with nitrogen for 20 minutes and refluxed overnight. After cooling to room temperature, the reaction mixture was filtered through a Celite® plug and eluted with dichlo-

Synthesis of 2-(3,5-dimethylphenyl)-5,7-diisobutylquinoline Chloro-bridged iridium dimer A mixture of 2-(3,5-dimethylphenyl)-5,7-diisobutylquinoline (4.38 g, 12.7 mmol), $IrCl_3 \cdot 4H_2O$ (2.14 g, 5.76 mmol), 2-ethoxyethanol (48 mL) and water (16 mL) was refluxed under nitrogen overnight. The reaction mixture was filtered and washed with methanol. After vacuum drying, 1.66 g of dimer was obtained. The dimer was used for the next step without further purification.

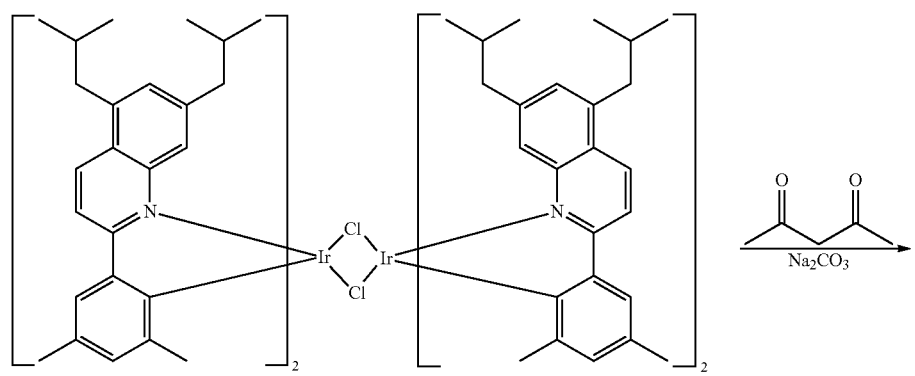

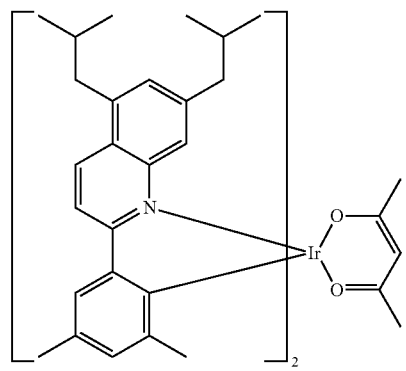

Synthesis of Compound 1:

2-(3,5-Dimethylphenyl)-5,7-diisobutylquinoline iridium dimer (1.66 g, 0.905 mmol), pentane-2,4-dione (0.905 g, 9.05 mmol), K$_2$CO$_3$ (1.25 g, 9.05 mmol) and 2-ethoxyethanol (80 mL) were stirred at room temperature for 24 hours. The precipitate was filtered and washed with methanol. The solid was further purified by passing it through a silica gel plug (pretreated with 15% triethylamine in hexane) and eluted with 80:20 (v/v) (hexanes:dichloromethane). Iso-propanol and a minimum amount of DCM were added to the solid product obtained after column chromatography. The clear solution was concentrated down until the DCM was evaporated. After precipitation from 2-propanol, 1.6 g of product was obtained after filtration. The solid was sublimed under high vacuum at 200° C. to give Compound 1 (0.88 g, 49%).

Synthesis of Compound 2

Synthesis of Compound 2:

2-(3,5-dimethylphenyl)-5,7-diisobutylquinoline iridium dimer (1.1 g, 0.6 mmol), 2,8-dimethylnonane (1.1 g, 6.0 mmol), K$_2$CO$_3$ (1.1 g, 6.0 mmol) and 2-ethoxyethanol (60 mL) were stirred at room temperature for 24 hours. The precipitate was filtered and washed with methanol. The solid was further purified by passing it through a silica gel plug (pretreated with 15% triethylamine in hexane) and eluted with 80:20 (v/v) (hexanes:dichloromethane). Iso-propanol and a minimum amount of DCM were added to the solid product obtained after column chromatography. The clear solution was concentrated down until DCM was evaporated. After precipitation from 2-propanol, 0.6 g (47%) of product was obtained after filtration. The solid was sublimed under high vacuum at 220° C. to give Compound 2 (0.5 g).

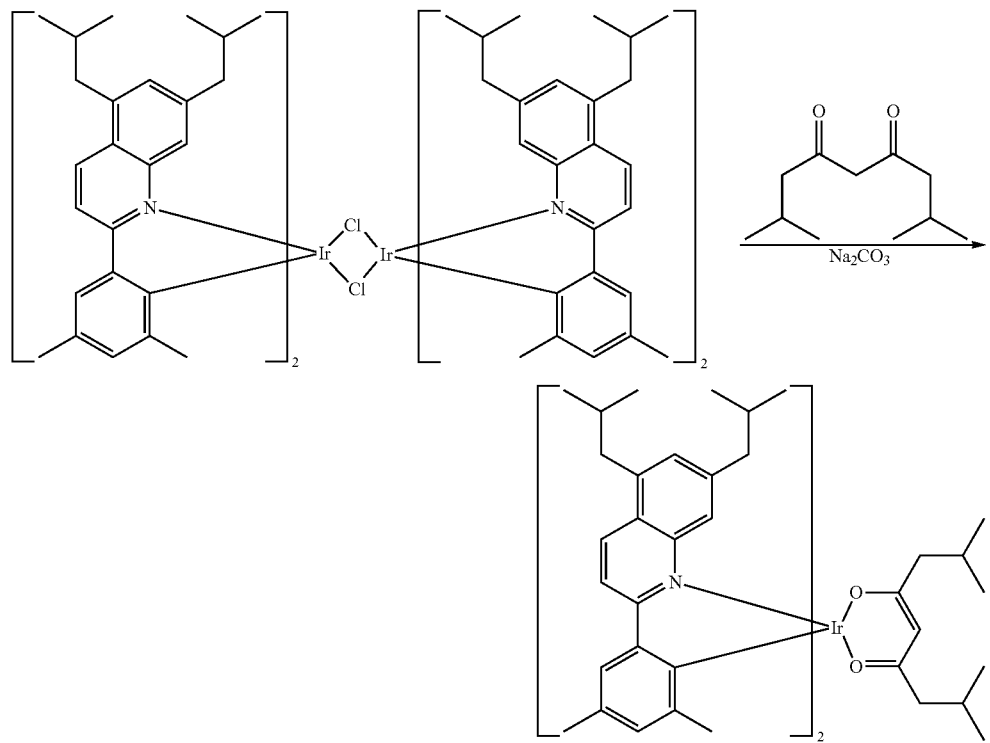

Synthesis of Compound 21

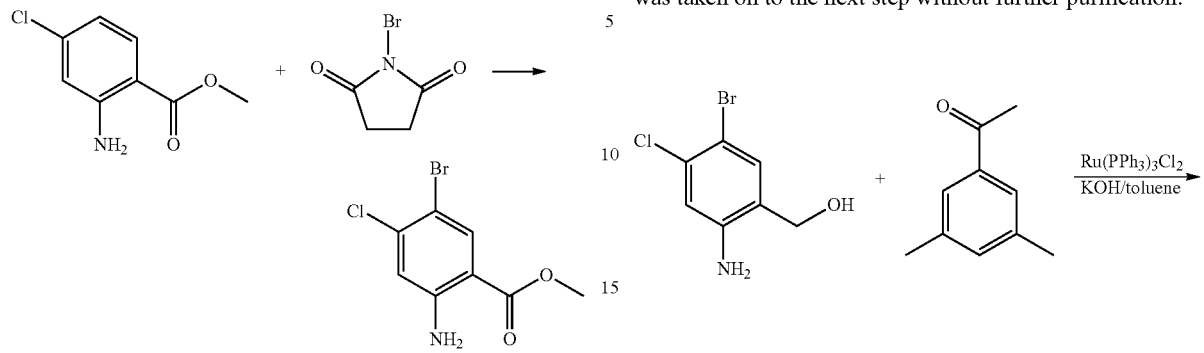

Synthesis of methyl 2-amino-5-bromo-4-chlorobenzoate

To a solution of methyl 2-amino-4-chlorobenzoate (20.0 g, 108 mmol) in DMF (200 mL) was added N-bromosuccinimide (19.2 g, 108 mmol) in one portion and stirred overnight at room temperature. The resulting solids were filtered off and dissolved in toluene, dried with $Na_2SO_4$, and concentrated to give methyl 2-amino-5-bromo-4-chlorobenzoate (26.47 g, 93%)

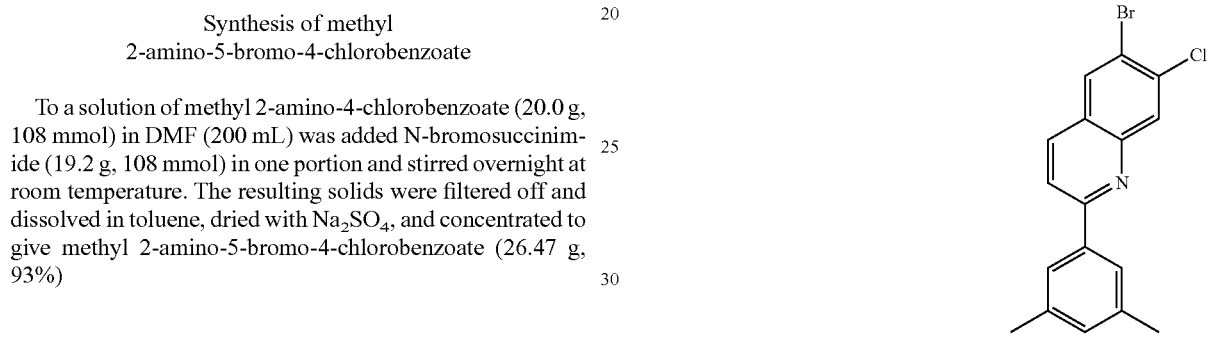

Synthesis of (2-amino-5-bromo-4-dichlorophenyl)methanol

A mixture of 28.5 mL of 2.0 M lithium aluminum hydride in tetrahydrofuran and tetrahydrofuran (180 mL) in a 1 L 2 neck round bottom flask was cooled to −78° C. A solution of methyl 2-amino-5-bromo-4-chlorobenzoate (13.7 g, 51.8 mmol) in tetrahydrofuran (140 mL) was rapidly added and allowed to warm to room temperature. After stirring at room temperature for 2 hours the reaction was quenched with saturated aqueous. $Na_2SO_4$ (16.8 mL) followed by solid $Na_2SO_4$ (10.5 g). The resulting salts were filtered through a plug of Celite® and the filter cake was washed with methanol. The filtrate was concentrated to give 2-amino-5-bromo-4-dichlorophenyl)methanol (16.4 g, 99%) as a yellow solid, which was taken on to the next step without further purification.

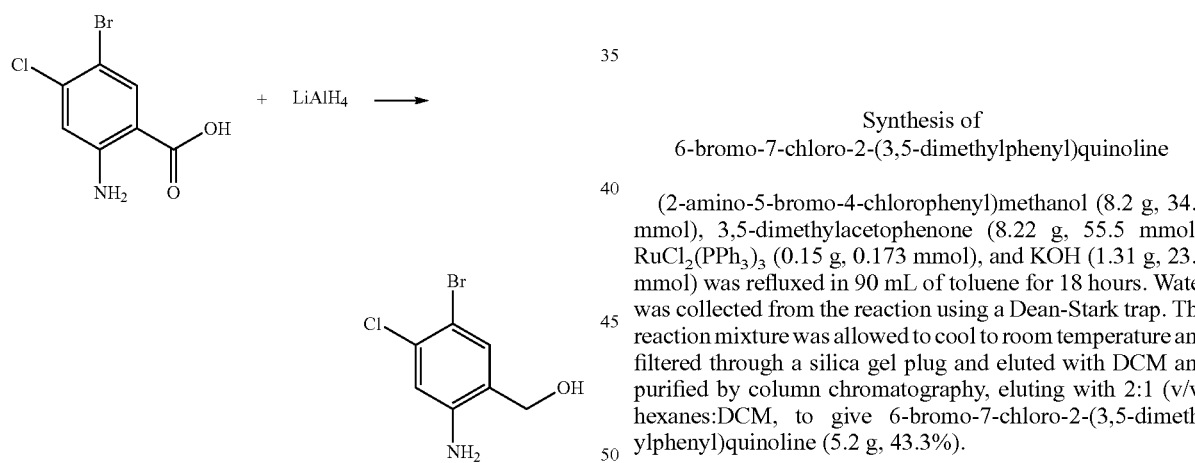

Synthesis of 6-bromo-7-chloro-2-(3,5-dimethylphenyl)quinoline (2-amino-5-bromo-4-chlorophenyl)methanol (8.2 g, 34.7 mmol), 3,5-dimethylacetophenone (8.22 g, 55.5 mmol), $RuCl_2(PPh_3)_3$ (0.15 g, 0.173 mmol), and KOH (1.31 g, 23.4 mmol) was refluxed in 90 mL of toluene for 18 hours. Water was collected from the reaction using a Dean-Stark trap. The reaction mixture was allowed to cool to room temperature and filtered through a silica gel plug and eluted with DCM and purified by column chromatography, eluting with 2:1 (v/v) hexanes:DCM, to give 6-bromo-7-chloro-2-(3,5-dimethylphenyl)quinoline (5.2 g, 43.3%).

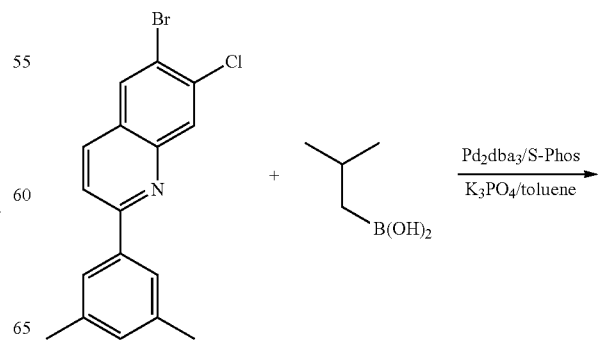

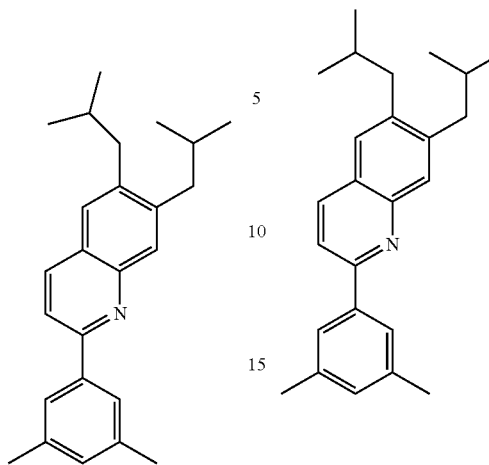

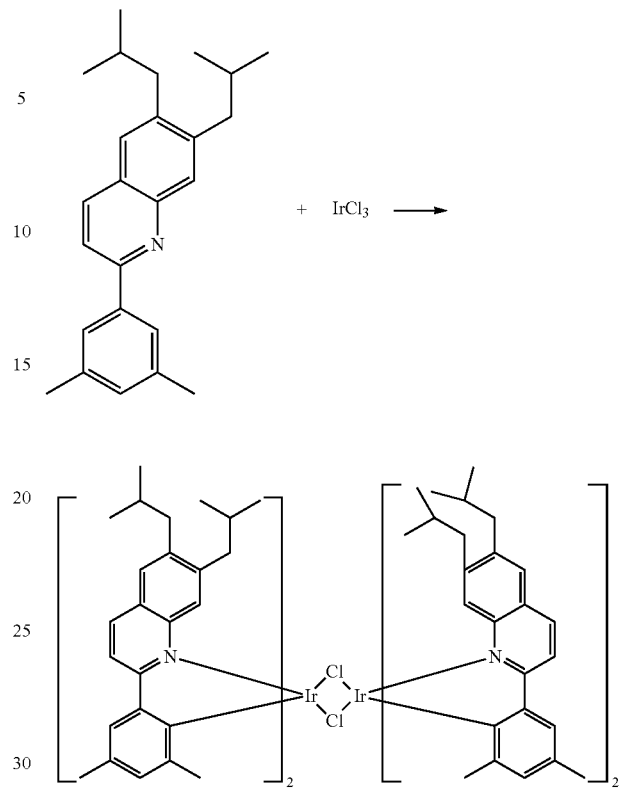

Synthesis of 2-(3,5-dimethylphenyl)-6,7-diisobutylquinoline

6-Bromo-7-chloro-2-(3,5-dimethylphenyl)quinoline (5.2 g, 15.0 mmol), isobutylboronic acid (6.12 g, 60.0 mmol), dicyclohexyl(2',6'-dimethoxy-[1,1'-biphenyl]-2-yl)phosphine (0.99 g, 2.4 mmol), Pd$_2$(dba)$_3$ (0.549 g, 0.60 mmol), potassium phosphate monohydrate (34.5 g, 150 mmol) and 2 mL of water were mixed in 240 mL of toluene. The system was degassed with nitrogen for 20 minutes and refluxed overnight. After cooling to room temperature, the reaction mixture was filtered through a Celite® plug and eluted with dichloromethane. The product was purified by column chromatography, eluting with 2:1 (v/v) hexanes:DCM, to give 2-(3,5-dimethylphenyl)-6,7-diisobutylquinoline (3.43 g, 66%).

Synthesis of 2-(3,5-dimethylphenyl)-6,7-diisobutylquinoline iridium dimer

A mixture of 2-(3,5-dimethylphenyl)-6,7-diisobutylquinoline (3.43 g, 9.9 mmol), IrCl$_3$.4H$_2$O (1.60 g, 4.32 mmol), ethoxyethanol (85 mL) and water (28 mL) was refluxed under nitrogen overnight. The reaction mixture was filtered and washed with methanol. 2-(3,5-Dimethylphenyl)-6,7-diisobutylquinoline iridium dimer (1.4 g, 35.4%) was obtained after vacuum drying. The dimer was used for the next step without further purification.

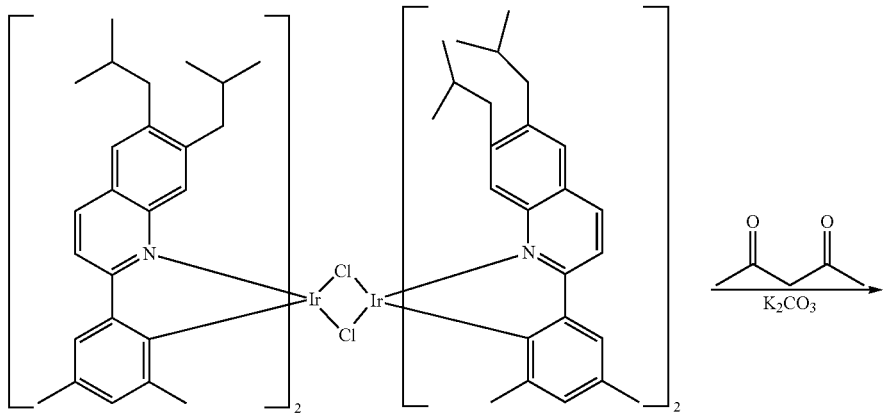

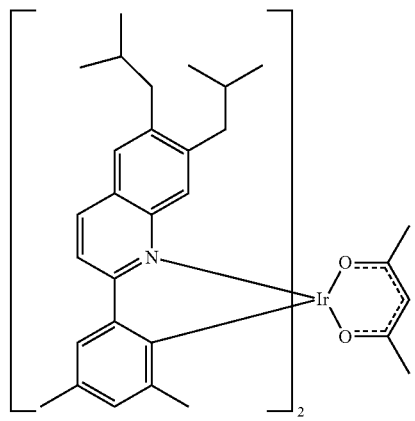

Synthesis of Compound 21:

2-(3,5-dimethylphenyl)-6,7-diisobutylquinoline Iridium dimer (1.4 g, 0.764 mmol), pentane-2,4-dione (0.764 g, 7.64 mmol), $K_2CO_3$ (1.06 g, 7.64 mmol) and 2-ethoxyethanol (100 mL) were stirred at room temperature for 24 hours. The precipitate was filtered and washed with methanol. The solid was further purified by passing it through a silica gel plug and eluted with 80:20 (v/v) (hexanes:dichloromethane). 2-Propanol was added to the filtrate. The filtrate was concentrated (but not to dryness), and then filtered to obtain (0.93 g, 62%) of Compound 21, which was confirmed by LC-MS.

Synthesis of Compound 11

Compound 11 was prepared by a similar synthetic route as Compound 21.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

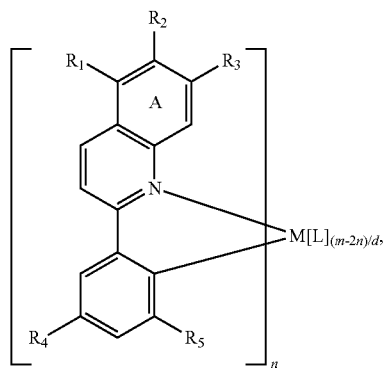

Formula II;

wherein M is Ir;
wherein L is a second ligand, wherein L is

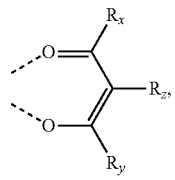

and wherein $R_x$, $R_y$, and $R_z$, are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein d is 2;

wherein m is 6;

wherein n is 2;

wherein each of $R_1$, $R_2$, and $R_3$ is independently selected from the group consisting of hydrogen, deuterium, alkyl, silyl, germyl, cycloalkyl, and combinations thereof;

wherein at least two of $R_1$, $R_2$, and $R_3$ are not hydrogen or deuterium;

wherein at least one of $R_1$, $R_2$, and $R_3$ is selected from the group consisting of $CH_2C(CH_3)_3$, silyl, germyl, and cycloalkyl;

wherein the sum of the number of carbon atoms in $R_1$, $R_2$, and $R_3$ is at least 4;

wherein any carbon atom in $R_1$, $R_2$, or $R_3$ attached directly to ring A is a primary, a secondary, or a tertiary carbon atom; and wherein $R_4$ and $R_5$ are alkyl.

2. The compound of claim 1, wherein $R_x$, $R_y$, and $R_z$ are independently selected from the group consisting of alkyl, hydrogen, deuterium, and combinations thereof.

3. The compound of claim 1, wherein $R_z$ is hydrogen or deuterium, and $R_x$ and $R_y$ are independently selected from the group consisting of methyl, $CH(CH_3)_2$, and $CH_2CH(CH_3)_2$.

4. The compound of claim 1, wherein the compound has the formula:

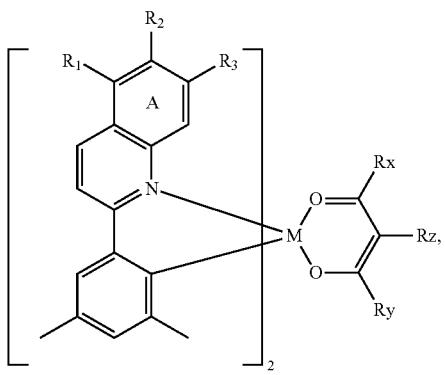

Formula IV.

5. The compound of claim 1, wherein $R_1$ and $R_3$ are alkyl and at least one is $CH_2C(CH_3)_3$.

6. The compound of claim 1, wherein $R_1$ and $R_2$ are alkyl and at least one is $CH_2C(CH_3)_3$.

7. The compound of claim 1, wherein $R_2$ and $R_3$ are alkyl and at least one is $CH_2C(CH_3)_3$.

8. The compound of claim 1, wherein at least one of $R_1$, $R_2$, and $R_3$ is silyl or germyl.

9. The compound of claim 1, wherein at least one of $R_1$, $R_2$ and $R_3$ is selected from the group consisting of $CH_2C(CH_3)_3$, cyclopentyl, and cyclohexyl.

10. A first device comprising a first organic light emitting device, comprising:
   an anode;
   a cathode; and
   an organic layer, disposed between the anode and the cathode, comprising a compound having the formula:

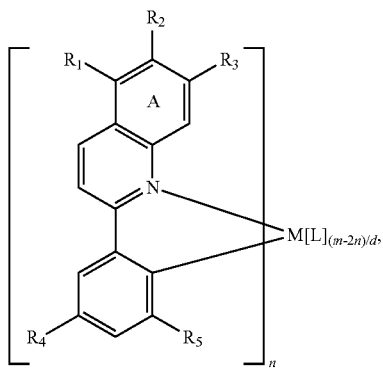

Formula II;

wherein M is Ir;
wherein L is a second ligand, wherein L is

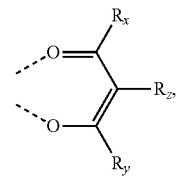

and
wherein $R_x$, $R_y$, and $R_z$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein d is 2;
wherein m is 6;
wherein n is 2;
wherein each of $R_1$, $R_2$, and $R_3$ is independently selected from the group consisting of hydrogen, deuterium, alkyl, silyl, germyl, cycloalkyl, and combinations thereof;
wherein at least two of $R_1$, $R_2$, and $R_3$ are not hydrogen or deuterium;
wherein at least one of $R_1$, $R_2$, and $R_3$ is selected from the group consisting of $CH_2C(CH_3)_3$, silyl, germyl, and cycloalkyl;
wherein the sum of the number of carbon atoms in $R_1$, $R_2$, and $R_3$ is at least 4;
wherein any carbon atom in $R_1$, $R_2$, or $R_3$ attached directly to ring A is a primary, a secondary, or a tertiary carbon atom; and
wherein $R_4$ and $R_5$ are alkyl.

11. The first device of claim 10, wherein the first device is a consumer product.

12. The first device of claim 10, wherein the first device is an organic light-emitting device.

13. The first device of claim 10, wherein the first device comprises a lighting panel.

14. The first device of claim 10, wherein the organic layer is an emissive layer and the compound is an emissive dopant.

15. The first device of claim 10, wherein the organic layer further comprises a host.

16. The first device of claim 15, wherein the host is a metal 8-hydroxyquinolate.

17. The first device of claim 16, wherein the host is:

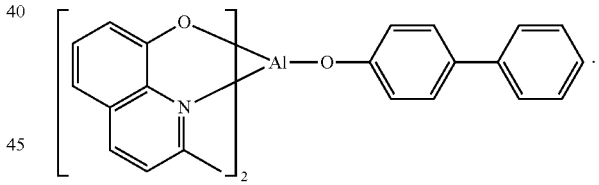

18. A compound having the formula:

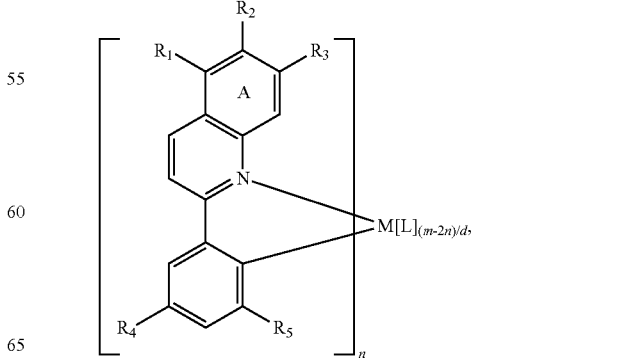

Formula II;

wherein M is Ir;

wherein L is a second ligand, wherein L is

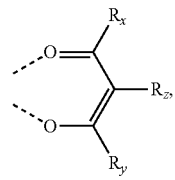

and wherein $R_x$, $R_y$, and $R_z$, are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein d is 2;

wherein m is 6;

wherein n is 2;

wherein each of $R_1$, $R_2$, and $R_3$ is independently selected from the group consisting of hydrogen, deuterium, alkyl, silyl, germyl, cycloalkyl, and combinations thereof;

wherein at least two of $R_1$, $R_2$, and $R_3$ are not hydrogen or deuterium;

wherein at least one of $R_1$, $R_2$, and $R_3$ is selected from the group consisting of silyl, germyl, and cycloalkyl;

wherein the sum of the number of carbon atoms in $R_1$, $R_2$, and $R_3$ is at least 4;

wherein any carbon atom in $R_1$, $R_2$, or $R_3$ attached directly to ring A is a primary, a secondary, or a tertiary carbon atom; and wherein $R_4$ and $R_5$ are alkyl.

19. The compound of claim 18, wherein at least one of $R_1$, $R_2$ and $R_3$ is silyl.

20. The compound of claim 18, wherein at least one of $R_1$, $R_2$ and $R_3$ is germyl.

21. The compound of claim 18, wherein at least one of $R_1$, $R_2$ and $R_3$ is cycloalkyl.

22. The compound of claim 18, wherein the compound is selected from the group consisting of:

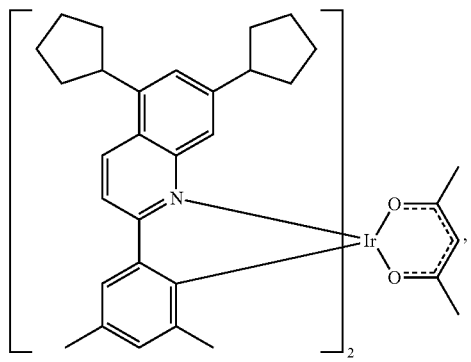

Compound 10

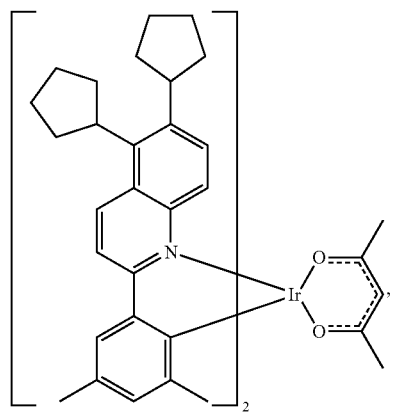

Compound 20

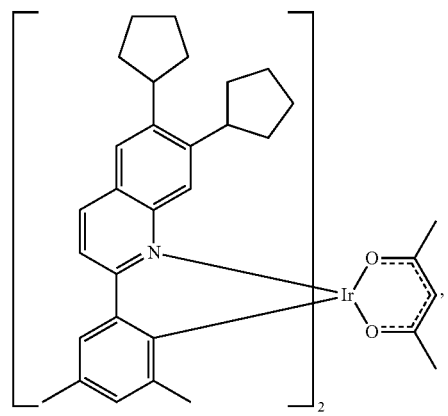

Compound 28

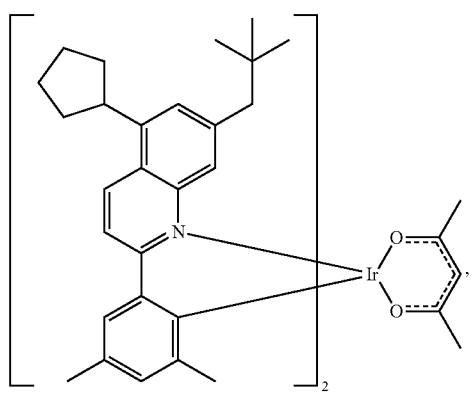

Compound 36

Compound 37
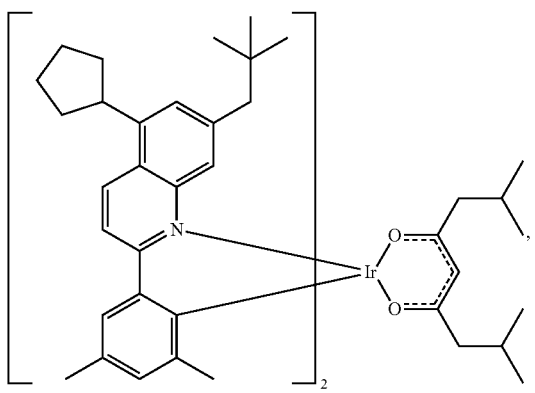
Compound 38
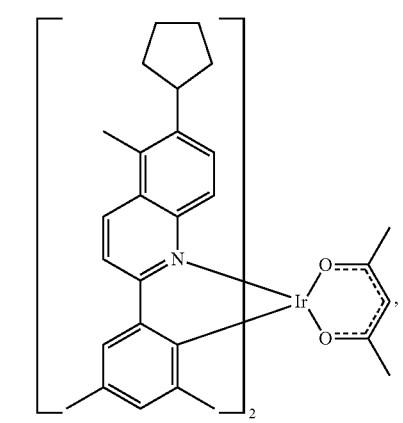
Compound 39
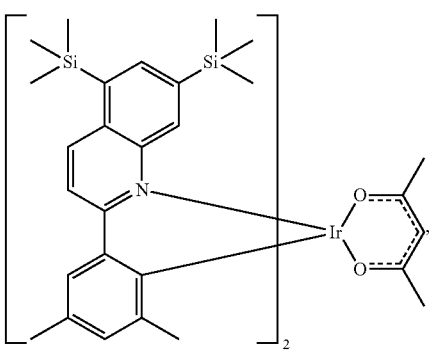
Compound 40
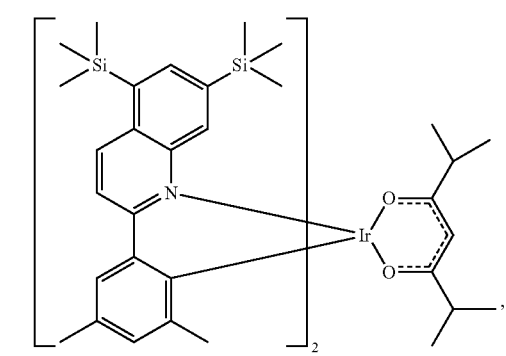
Compound 41
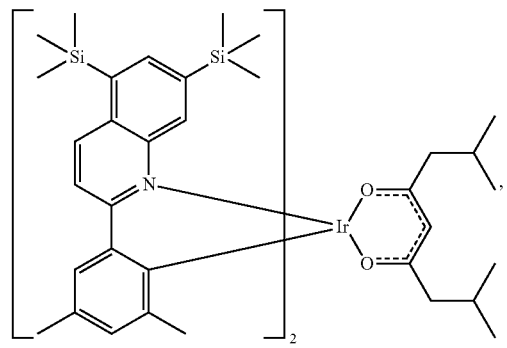
Compound 42
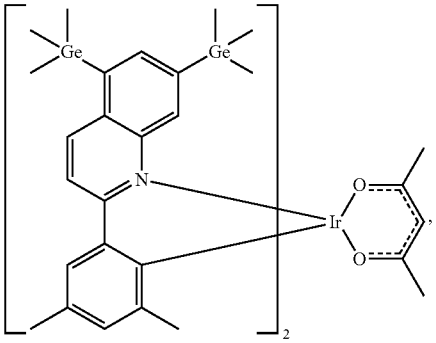
Compound 43
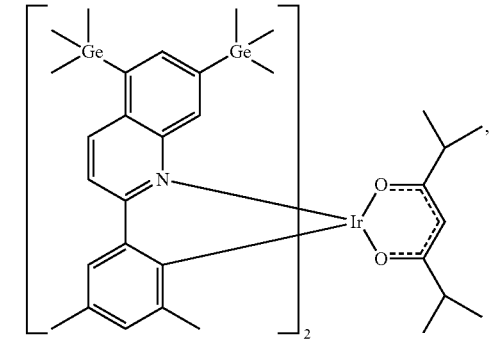
Compound 44
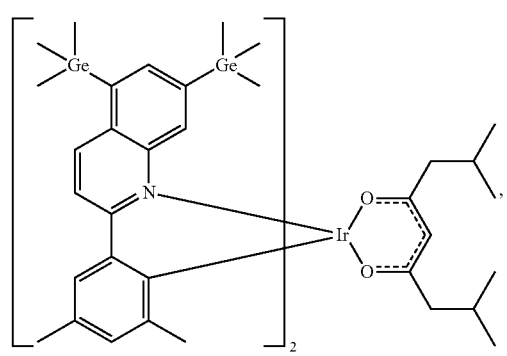

Compound 45
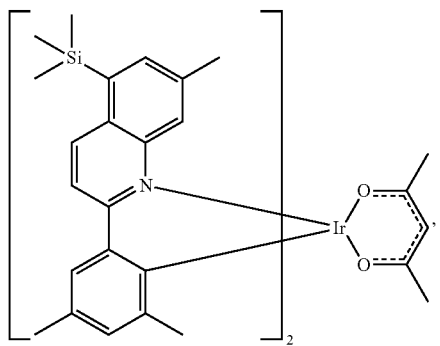
Compound 46
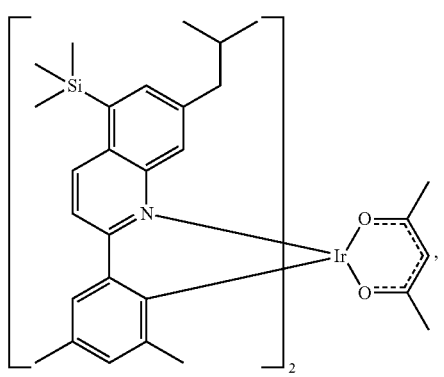
Compound 47
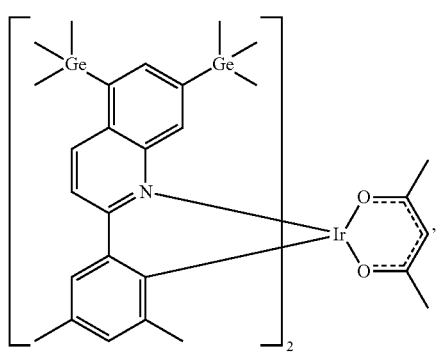
Compound 48
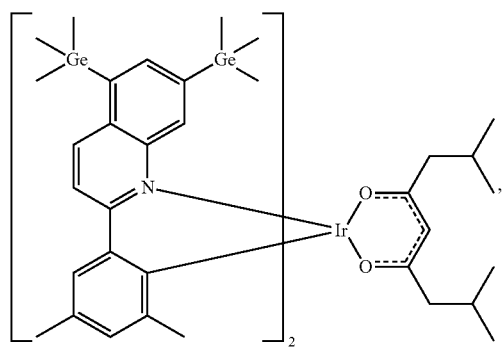
Compound 49
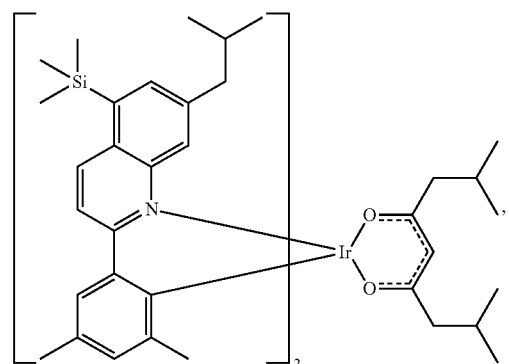
Compound 50
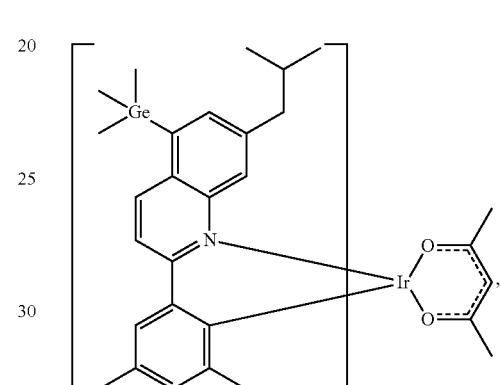
Compound 51
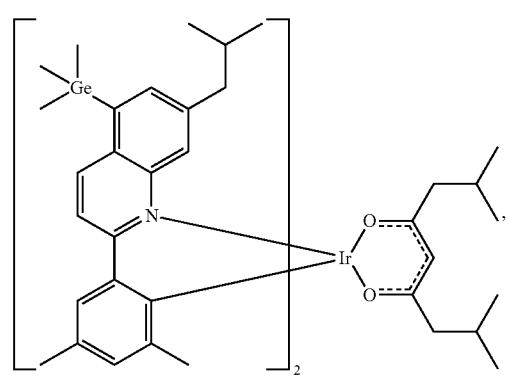
Compound 52
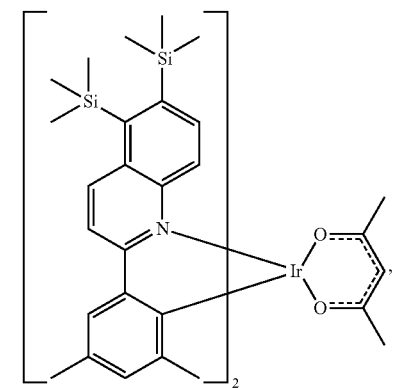

Compound 53
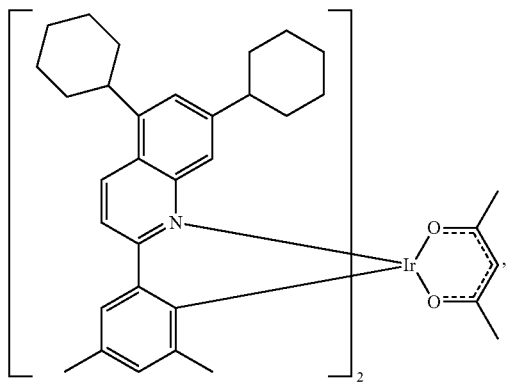
Compound 54
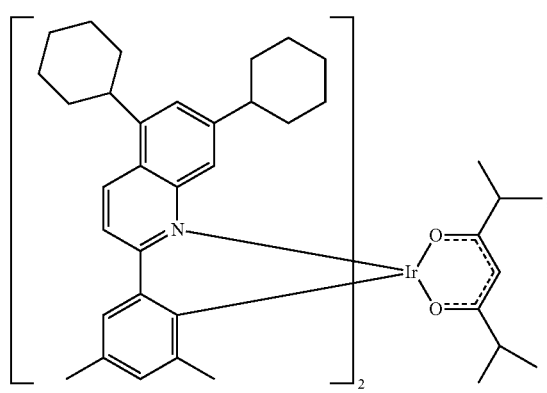
Compound 55
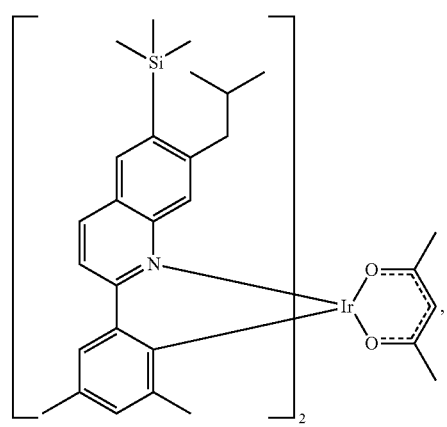
Compound 56
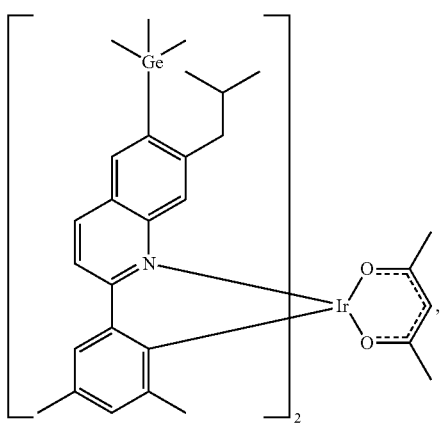
Compound 57
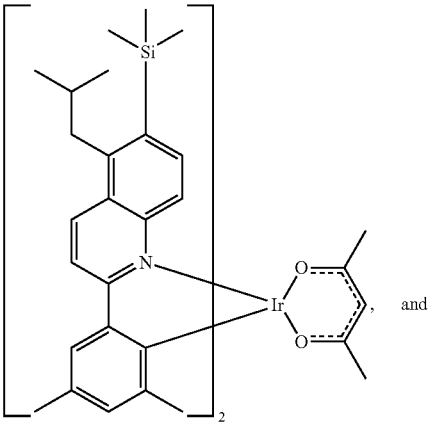
Compound 58
23. The compound of claim 1, wherein the compound is selected from the group consisting of:

Compound 7
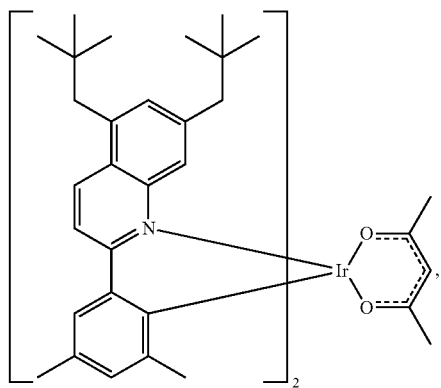
Compound 8
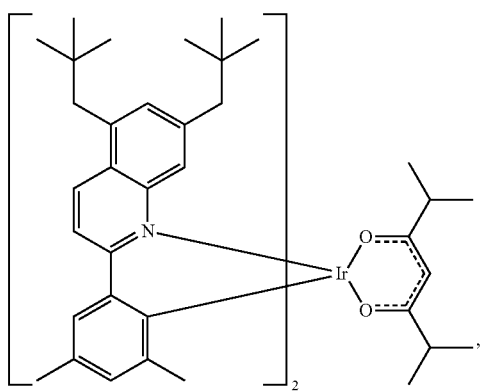
Compound 9
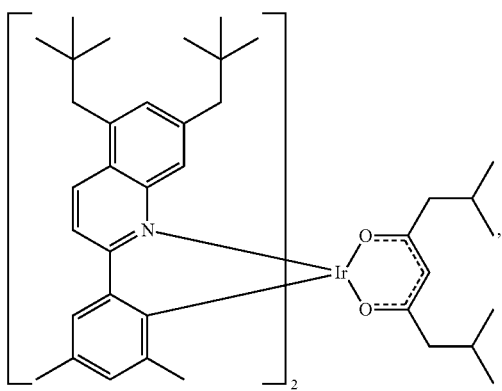
Compound 10
Compound 18
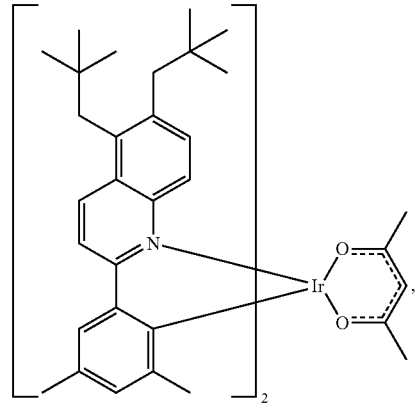
Compound 19
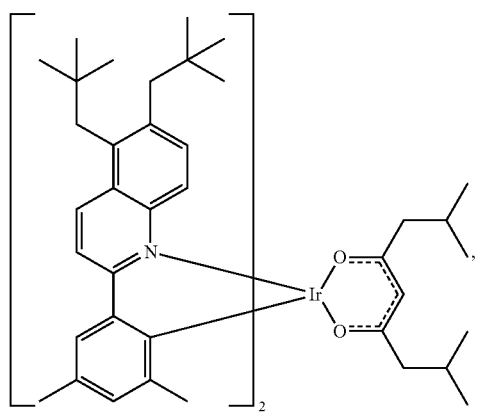
Compound 20
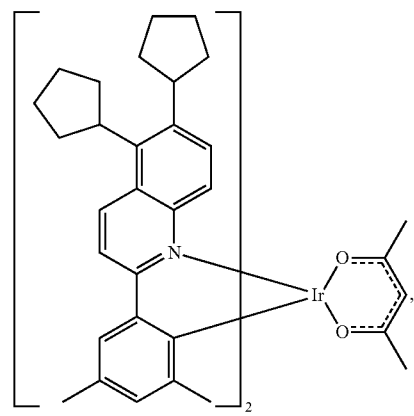

Compound 26
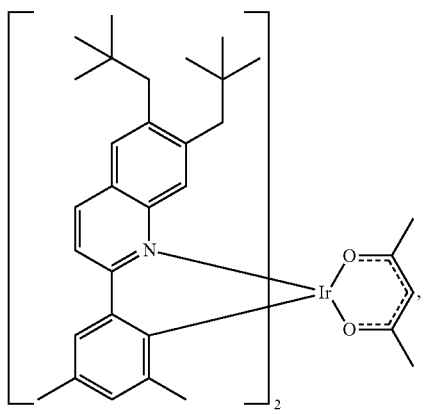
Compound 27
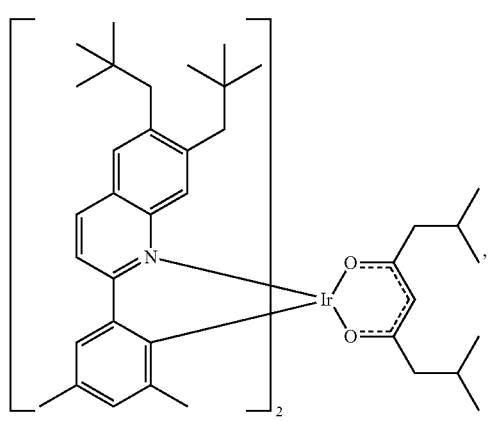
Compound 28
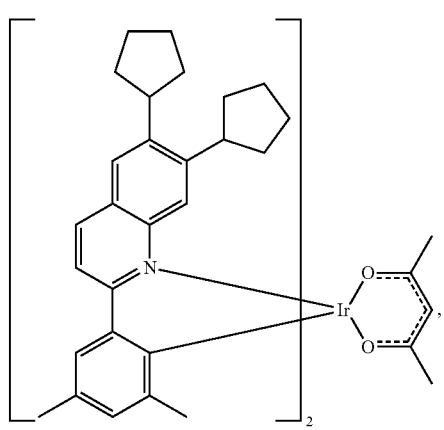
Compound 35
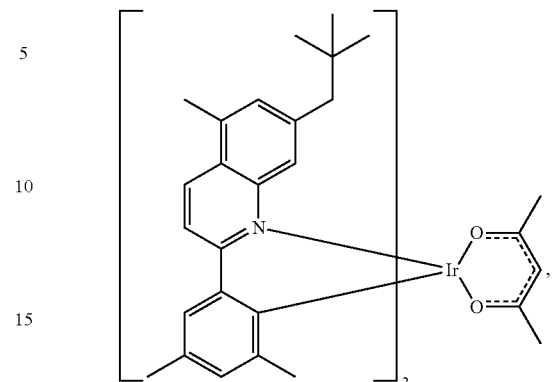
Compound 36
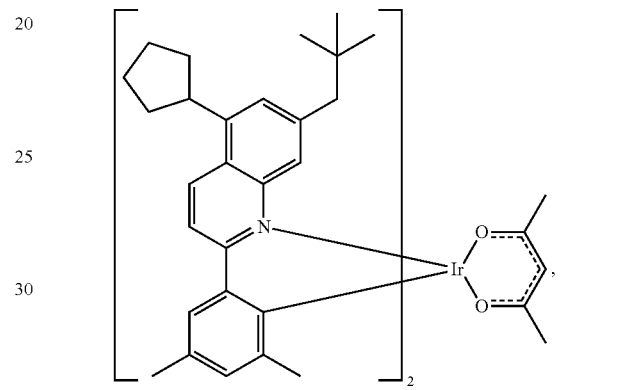
Compound 37
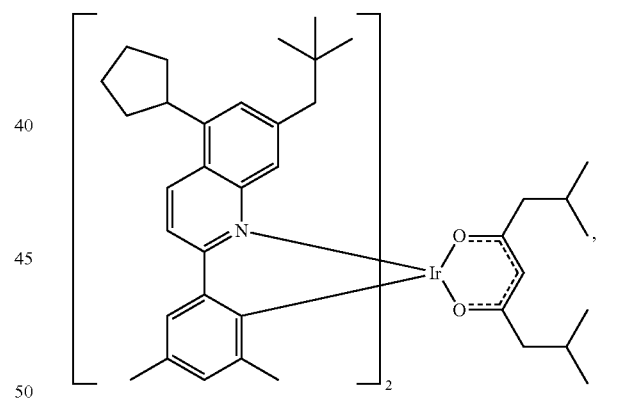
Compound 38
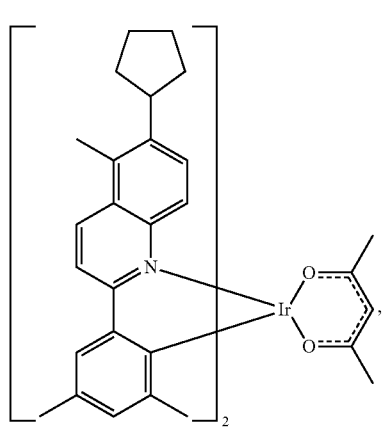

-continued
Compound 53
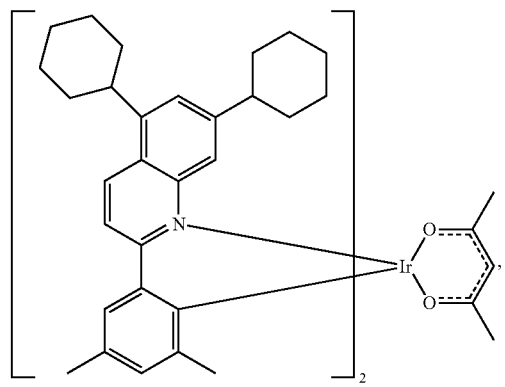
and
Compound 54
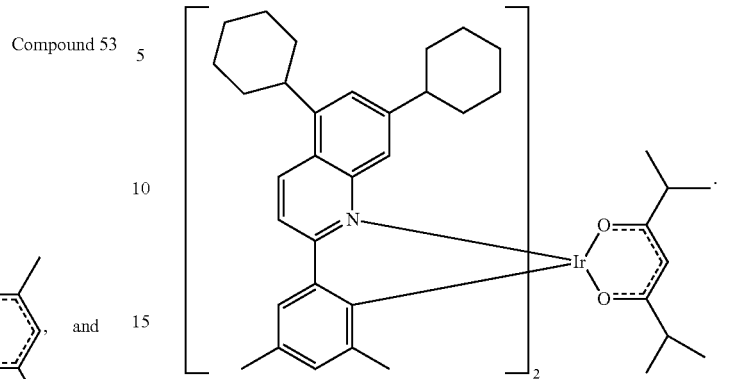
* * * * *